United States Patent
Mucha et al.

(10) Patent No.: US 11,029,314 B2
(45) Date of Patent: Jun. 8, 2021

(54) METHODS FOR DIAGNOSIS, DIFFERENTIATION AND MONITORING USING URINE PROTEINS AS MARKERS IN IGA NEPHROPATHY

(71) Applicants: WARSZAWSKI UNIWERSYTET MEDYCZNY, Warsaw (PL); INSTYTUT BIOCHEMII I BIOFIZYKI POLSKIEJ AKADEMII NAUK, Warsaw (PL)

(72) Inventors: Krzysztof Mucha, Warsaw (PL); Leszek Paczek, Warsaw (PL); Radoslaw Zagozdzon, Truskaw (PL); Bartosz Foroncewicz, Warsaw (PL); Michal Dadlez, Warsaw (PL); Magdalena Bakun, Warsaw (PL); Jan Piwowarski, Warsaw (PL); Tomas Pilzys, Vilnius (LT); Michal Marcinkowski, Zagan (PL); Damian Garbicz, Radomysl (PL); Elzbieta Grzesiuk, Warsaw (PL); Michal Florczak, Warsaw (PL)

(73) Assignees: INSTYTUT BIOCHEMII I BIOFIZYKI POLSKIEJ AKADEMII NAUK, Warsaw (PL); WARSZAWSKI UNIWERSYTET MEDYCZNY, Warsaw (PL)

( * ) Notice: Subject to any disclaimer, the term of this patent is extended or adjusted under 35 U.S.C. 154(b) by 0 days.

(21) Appl. No.: 16/308,591

(22) PCT Filed: Jun. 12, 2017

(86) PCT No.: PCT/IB2017/053479
§ 371 (c)(1),
(2) Date: Dec. 10, 2018

(87) PCT Pub. No.: WO2017/212463
PCT Pub. Date: Dec. 14, 2017

(65) Prior Publication Data
US 2019/0339284 A1 Nov. 7, 2019

(30) Foreign Application Priority Data
Jun. 10, 2016 (PL) .................................... P-417515

(51) Int. Cl.
*G01N 33/53* (2006.01)
*G01N 33/68* (2006.01)
*G01N 33/493* (2006.01)

(52) U.S. Cl.
CPC ....... *G01N 33/6827* (2013.01); *G01N 33/493* (2013.01); *G01N 33/6848* (2013.01); *G01N 2800/347* (2013.01)

(58) Field of Classification Search
None
See application file for complete search history.

(56) References Cited

U.S. PATENT DOCUMENTS

| 8,927,220 B2 | 1/2015 | Baek et al. | |
| 2010/0184049 A1 | 7/2010 | Goodison et al. | |
| 2011/0236913 A1* | 9/2011 | Baek ..................... | G01N 33/564 435/7.92 |
| 2014/0038203 A1 | 2/2014 | Arthur et al. | |
| 2014/0186332 A1* | 7/2014 | Ezrin .................... | G01N 33/689 424/130.1 |
| 2015/0141273 A1 | 5/2015 | Bosch et al. | |
| 2016/0061845 A1 | 3/2016 | Bennett et al. | |
| 2018/0171337 A1* | 6/2018 | O'Neill .............. | A61K 47/6807 |

FOREIGN PATENT DOCUMENTS

| CN | 102590491 A | 7/2012 |
| EP | 2535718 A2 | 12/2012 |
| KR | 100930025 B1 | 12/2009 |
| PL | 415033 A1 | 6/2017 |
| WO | 03002757 A1 | 1/2003 |
| WO | 2011035323 A1 | 3/2011 |
| WO | 2013152989 A2 | 10/2013 |
| WO | 2015025975 A1 | 2/2015 |
| WO | 2017093920 A1 | 6/2017 |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*

Torzewski et al., Animal Models of C-Reactive Protein, Hindawl Publishing Corporation, Mediators of Inflammation, vol. 2014, Article ID 683598, 2014, pp. 1-7. (Year: 2014).*

Kalantari et al., Human Urine Proteomics: Analytical Techniques and Clinical Applications in Renal Diseases, International Journal of Proteomics, vol. 2015, Jan. 2016, pp. 1-17. (Year: 2016).*

M. T. Rocchetti et al: "Association of Urinary Laminin G-Like 3 and Free K Light Chains with Disease Activity and Histological Injury in IgA Nephropathy", Clinical Journal of the American Society of Nephrology, pp. 115-1125, vol. 8, No. 7 (Apr. 2013).

Kzysztof Mucha et al: "Complement components, proteolysis-related, and cell communication-related proteins detected in urine proteomics are associated with IgA nephropathy", Polskie Archiwum Medycyny Wewnetrznej, pp. 380-386, vol. 124, No. 7-8 (Jan. 2014).

(Continued)

*Primary Examiner* — Gary Counts

(74) *Attorney, Agent, or Firm* — Browdy and Neimark, PLLC

(57) ABSTRACT

A method for diagnosis of IgA nephropathy is provided using a combination of alpha-1B-glycoprotein (A1BG) or a truncated fragment thereof having a molecular weight of 13-60 kDa, orosomucoid 1 (ORMI), and Ig lambda-2 chain C regions (IGLC2) as protein markers in a urine sample from a subject.

4 Claims, 9 Drawing Sheets

Specification includes a Sequence Listing.

(56) References Cited

OTHER PUBLICATIONS

Justyna Siwy et al: "Sa0039 Urlnary Proteomics Identifies Marker Peptides in Patients With Anca-Associated Vasculitis (AAV), IGA Nephropathy (IGAN), and Henoch-Schonlein Purpura Nephritis (HSPN)", Nephrology Dialysis Transplantation, pp. iii40-iii41, vol. 30, No. Suppl. 3 (May 2015).
Hiroyuki Yokota et al: "Absence of Increased [alpha]I-Microglobulin in IGA Nephropathy Proteinuria", Molecular & Cellular Proteomics, pp. 438-744, vol. 6, No. 4 (Apr. 2007).
Park M-R et al: "Establishment of a 2-0 Human Urinary Proteomic Map in IGA Nephropathy", Proteomics, pp. 1066-1076, vol. 6, No. 3 (Feb. 2006).
Kilis-Pstruslnska, "Carnosine, carnosinase and kidney diseases", Postepy Hig Med Dosw, pp. 215-221, vol. 66 (2012).
Piyaphanee N et al.,"Discovery and initial validation of "alpha" 1-B glycoprotein fragmentation as a differential urinary biomarker in pediatric steroid-resistant nephrotic syndrome", Proteomics Clin Appl., pp. 334-342, vol. 5, No. 5-6 (Mar. 2011).
Aebersold et al., "Mass spectrometry-based proteomics", Nature, pp. 198-207, vol. 422, No. 6928 (Mar. 2003).
Yates., "Mass Spectral Analysis in Proteomics", Annu. Rev. Biophys. Biomol. Struct., pp. 297-316, vol. 33 (2004).
Wang et al., "Ultrasensitive microfluidic solid-phase ELISA using an actuatable microwell-patterned PDMS chip", Lab Chip, pp. 4190-4197, vol. 21 (2013).
Gwendolyn A J., "Western Blotting using Capillary Electrophoresis", Anal Chem., pp. 1350-1355, vol. 83, No. 4 (Feb. 2011).
Pachel C et al., "Inhibition of Platelet GPVI Protects Against Myocardial Ischemia-Reperfusion Injury", Arterioscler Thromb Vasc Biol, pp. 629-635, vol. 36, No. 4 (Feb. 2016).
Devi et al.,"Platelet Recruitment to the Inflamed Glomerulus Occurs via an "alpha"IIb"beta"3/GPVI-Dependent Pathway", The American Journal of Pathology, pp. 1131-1142, vol. 177, No. 3, (Sep. 2010).

* cited by examiner

Fig. 7

A1BG-TF, ORM1-TF, IGLC2-TF, A1BG-ORM1, A1BG-IGLC2, ORM1-IGLC2, A1BG-ORM1-TF, A1BG-IGLC2-TF, ORM1-IGLC2-TF, A1BG-ORM1-IGLC2, A1BG-ORM1-IGLC2-TF

SEQUENCE LISTING

```
<160> NUMBER OF SEQ ID NOS: 158

<210> SEQ ID NO 1
<211> LENGTH: 6
<212> TYPE: PRT
<213> ORGANISM: Homo sapiens
<220> FEATURE:
<223> OTHER INFORMATION: Alpha-1B-glycoprotein peptide

<400> SEQUENCE: 1

Ser Leu Pro Ala Pro Trp
1               5

<210> SEQ ID NO 2
<211> LENGTH: 6
<212> TYPE: PRT
<213> ORGANISM: Homo sapiens
<220> FEATURE:
<223> OTHER INFORMATION: Alpha-1B-glycoprotein peptide

<400> SEQUENCE: 2

Ile Thr Pro Gly Leu Lys
1               5

<210> SEQ ID NO 3
<211> LENGTH: 7
<212> TYPE: PRT
<213> ORGANISM: Homo sapiens
<220> FEATURE:
<223> OTHER INFORMATION: Alpha-1B-glycoprotein peptide

<400> SEQUENCE: 3

Gly Val Thr Phe Leu Leu Arg
1               5

<210> SEQ ID NO 4
<211> LENGTH: 7
<212> TYPE: PRT
<213> ORGANISM: Homo sapiens
<220> FEATURE:
<223> OTHER INFORMATION: Alpha-1B-glycoprotein peptide

<400> SEQUENCE: 4

Ser Trp Val Pro His Thr Phe
1               5

<210> SEQ ID NO 5
<211> LENGTH: 8
<212> TYPE: PRT
<213> ORGANISM: Homo sapiens
<220> FEATURE:
<223> OTHER INFORMATION: Alpha-1B-glycoprotein peptide

<400> SEQUENCE: 5
```

Leu Leu Glu Leu Thr Gly Pro Lys
1               5

<210> SEQ ID NO 6
<211> LENGTH: 8
<212> TYPE: PRT
<213> ORGANISM: Homo sapiens
<220> FEATURE:
<223> OTHER INFORMATION: Alpha-1B-glycoprotein peptide

<400> SEQUENCE: 6

Ser Trp Ile Thr Pro Gly Leu Lys
1               5

<210> SEQ ID NO 7
<211> LENGTH: 11
<212> TYPE: PRT
<213> ORGANISM: Homo sapiens
<220> FEATURE:
<223> OTHER INFORMATION: Alpha-1B-glycoprotein peptide

<400> SEQUENCE: 7

Ala Thr Trp Ser Gly Ala Val Leu Ala Gly Arg
1               5                   10

<210> SEQ ID NO 8
<211> LENGTH: 11
<212> TYPE: PRT
<213> ORGANISM: Homo sapiens
<220> FEATURE:
<223> OTHER INFORMATION: Alpha-1B-glycoprotein peptide

<400> SEQUENCE: 8

Leu Glu Leu His Val Asp Gly Pro Pro Pro Arg
1               5                   10

<210> SEQ ID NO 9
<211> LENGTH: 12
<212> TYPE: PRT
<213> ORGANISM: Homo sapiens
<220> FEATURE:
<223> OTHER INFORMATION: Alpha-1B-glycoprotein peptide

<400> SEQUENCE: 9

Ser Leu Pro Ala Pro Trp Leu Ser Met Ala Pro Val
1               5                   10

<210> SEQ ID NO 10
<211> LENGTH: 12
<212> TYPE: PRT
<213> ORGANISM: Homo sapiens
<220> FEATURE:
<223> OTHER INFORMATION: Alpha-1B-glycoprotein peptide

<400> SEQUENCE: 10

Val Ala Pro Leu Ser Gly Val Asp Phe Gln Leu Arg
1               5                   10

<210> SEQ ID NO 11
<211> LENGTH: 12
<212> TYPE: PRT
<213> ORGANISM: Homo sapiens
<220> FEATURE:
<223> OTHER INFORMATION: Alpha-1B-glycoprotein peptide

<400> SEQUENCE: 11

```
Ile Phe Val Gly Pro Gln His Ala Gly Asn Tyr Arg
1               5                   10
```

<210> SEQ ID NO 12
<211> LENGTH: 12
<212> TYPE: PRT
<213> ORGANISM: Homo sapiens
<220> FEATURE:
<223> OTHER INFORMATION: Alpha-1B-glycoprotein peptide

<400> SEQUENCE: 12

```
His Gln Phe Leu Leu Thr Gly Asp Thr Gln Gly Arg
1               5                   10
```

<210> SEQ ID NO 13
<211> LENGTH: 10
<212> TYPE: PRT
<213> ORGANISM: Homo sapiens
<220> FEATURE:
<223> OTHER INFORMATION: Alpha-1B-glycoprotein peptide

<400> SEQUENCE: 13

```
Leu Glu Thr Pro Asp Phe Gln Leu Phe Lys
1               5                   10
```

<210> SEQ ID NO 14
<211> LENGTH: 12
<212> TYPE: PRT
<213> ORGANISM: Homo sapiens
<220> FEATURE:
<223> OTHER INFORMATION: Alpha-1B-glycoprotein peptide

<400> SEQUENCE: 14

```
Ser Gly Leu Ser Thr Gly Trp Thr Gln Leu Ser Lys
1               5                   10
```

<210> SEQ ID NO 15
<211> LENGTH: 13
<212> TYPE: PRT
<213> ORGANISM: Homo sapiens
<220> FEATURE:
<223> OTHER INFORMATION: Alpha-1B-glycoprotein peptide

<400> SEQUENCE: 15

```
Ser Met Ala Pro Val Ser Trp Ile Thr Pro Gly Leu Lys
1               5                   10
```

<210> SEQ ID NO 16
<211> LENGTH: 13
<212> TYPE: PRT
<213> ORGANISM: Homo sapiens
<220> FEATURE:
<223> OTHER INFORMATION: Alpha-1B-glycoprotein peptide

<400> SEQUENCE: 16

```
His Gly Glu Ser Ser Gln Val Leu His Pro Gly Asn Lys
1               5                   10
```

<210> SEQ ID NO 17
<211> LENGTH: 14
<212> TYPE: PRT
<213> ORGANISM: Homo sapiens
<220> FEATURE:
<223> OTHER INFORMATION: Alpha-1B-glycoprotein peptide

<400> SEQUENCE: 17

```
Ser Leu Pro Ala Pro Trp Leu Ser Met Ala Pro Val Ser Trp
```

```
1               5                   10
```

<210> SEQ ID NO 18
<211> LENGTH: 14
<212> TYPE: PRT
<213> ORGANISM: Homo sapiens
<220> FEATURE:
<223> OTHER INFORMATION: Alpha-1B-glycoprotein peptide

<400> SEQUENCE: 18

```
Leu Glu Leu His Val Asp Gly Pro Pro Pro Arg Pro Gln Leu
1               5                   10
```

<210> SEQ ID NO 19
<211> LENGTH: 14
<212> TYPE: PRT
<213> ORGANISM: Homo sapiens
<220> FEATURE:
<223> OTHER INFORMATION: Alpha-1B-glycoprotein peptide

<400> SEQUENCE: 19

```
His His Gly Glu Ser Ser Gln Val Leu His Pro Gly Asn Lys
1               5                   10
```

<210> SEQ ID NO 20
<211> LENGTH: 14
<212> TYPE: PRT
<213> ORGANISM: Homo sapiens
<220> FEATURE:
<223> OTHER INFORMATION: Alpha-1B-glycoprotein peptide

<400> SEQUENCE: 20

```
His Gln Phe Leu Leu Thr Gly Asp Thr Gln Gly Arg Tyr Arg
1               5                   10
```

<210> SEQ ID NO 21
<211> LENGTH: 15
<212> TYPE: PRT
<213> ORGANISM: Homo sapiens
<220> FEATURE:
<223> OTHER INFORMATION: Alpha-1B-glycoprotein peptide

<400> SEQUENCE: 21

```
Gly Val Ala Gln Glu Pro Val His Leu Asp Ser Pro Ala Ile Lys
1               5                   10                  15
```

<210> SEQ ID NO 22
<211> LENGTH: 15
<212> TYPE: PRT
<213> ORGANISM: Homo sapiens
<220> FEATURE:
<223> OTHER INFORMATION: Alpha-1B-glycoprotein peptide

<400> SEQUENCE: 22

```
Leu Glu Leu Ile Phe Val Gly Pro Gln His Ala Gly Asn Tyr Arg
1               5                   10                  15
```

<210> SEQ ID NO 23
<211> LENGTH: 15
<212> TYPE: PRT
<213> ORGANISM: Homo sapiens
<220> FEATURE:
<223> OTHER INFORMATION: Alpha-1B-glycoprotein peptide

<400> SEQUENCE: 23

```
Leu Glu Leu His Val Asp Gly Pro Pro Pro Arg Pro Gln Leu Arg
1               5                   10                  15
```

```
<210> SEQ ID NO 24
<211> LENGTH: 16
<212> TYPE: PRT
<213> ORGANISM: Homo sapiens
<220> FEATURE:
<223> OTHER INFORMATION: Alpha-1B-glycoprotein peptide

<400> SEQUENCE: 24

Ile Phe Phe His Leu Asn Ala Val Ala Leu Gly Asp Gly Gly His Tyr
1               5                   10                  15

<210> SEQ ID NO 25
<211> LENGTH: 16
<212> TYPE: PRT
<213> ORGANISM: Homo sapiens
<220> FEATURE:
<223> OTHER INFORMATION: Alpha-1B-glycoprotein peptide

<400> SEQUENCE: 25

Asn Leu Glu Leu Ile Phe Val Gly Pro Gln His Ala Gly Asn Tyr Arg
1               5                   10                  15

<210> SEQ ID NO 26
<211> LENGTH: 17
<212> TYPE: PRT
<213> ORGANISM: Homo sapiens
<220> FEATURE:
<223> OTHER INFORMATION: Alpha-1B-glycoprotein peptide

<400> SEQUENCE: 26

Thr Phe Glu Ser Glu Leu Ser Asp Pro Val Glu Leu Leu Val Ala Glu
1               5                   10                  15

Ser

<210> SEQ ID NO 27
<211> LENGTH: 20
<212> TYPE: PRT
<213> ORGANISM: Homo sapiens
<220> FEATURE:
<223> OTHER INFORMATION: Alpha-1B-glycoprotein peptidep

<400> SEQUENCE: 27

Gly Ala Ala Ala Asn Leu Glu Leu Ile Phe Val Gly Pro Gln His Ala
1               5                   10                  15

Gly Asn Tyr Arg
            20

<210> SEQ ID NO 28
<211> LENGTH: 20
<212> TYPE: PRT
<213> ORGANISM: Homo sapiens
<220> FEATURE:
<223> OTHER INFORMATION: Alpha-1B-glycoprotein peptide

<400> SEQUENCE: 28

Ser Leu Pro Ala Pro Trp Leu Ser Met Ala Pro Val Ser Trp Ile Thr
1               5                   10                  15

Pro Gly Leu Lys
            20

<210> SEQ ID NO 29
<211> LENGTH: 22
<212> TYPE: PRT
<213> ORGANISM: Homo sapiens
```

<220> FEATURE:
<223> OTHER INFORMATION: Alpha-1B-glycoprotein peptide

<400> SEQUENCE: 29

Thr Pro Gly Ala Ala Ala Asn Leu Glu Leu Ile Phe Val Gly Pro Gln
1               5                   10                  15

His Ala Gly Asn Tyr Arg
            20

<210> SEQ ID NO 30
<211> LENGTH: 22
<212> TYPE: PRT
<213> ORGANISM: Homo sapiens
<220> FEATURE:
<223> OTHER INFORMATION: Alpha-1B-glycoprotein peptide

<400> SEQUENCE: 30

Ser Trp Val Pro His Thr Phe Glu Ser Glu Leu Ser Asp Pro Val Glu
1               5                   10                  15

Leu Leu Val Ala Glu Ser
            20

<210> SEQ ID NO 31
<211> LENGTH: 25
<212> TYPE: PRT
<213> ORGANISM: Homo sapiens
<220> FEATURE:
<223> OTHER INFORMATION: Alpha-1B-glycoprotein peptide

<400> SEQUENCE: 31

Thr Val Arg Thr Pro Gly Ala Ala Ala Asn Leu Glu Leu Ile Phe Val
1               5                   10                  15

Gly Pro Gln His Ala Gly Asn Tyr Arg
            20                  25

<210> SEQ ID NO 32
<211> LENGTH: 37
<212> TYPE: PRT
<213> ORGANISM: Homo sapiens
<220> FEATURE:
<223> OTHER INFORMATION: Alpha-1B-glycoprotein peptide

<400> SEQUENCE: 32

Leu His Asp Asn Gln Asn Gly Trp Ser Gly Asp Ser Ala Pro Val Glu
1               5                   10                  15

Leu Ile Leu Ser Asp Glu Thr Leu Pro Ala Pro Glu Phe Ser Pro Glu
            20                  25                  30

Pro Glu Ser Gly Arg
        35

<210> SEQ ID NO 33
<211> LENGTH: 42
<212> TYPE: PRT
<213> ORGANISM: Homo sapiens
<220> FEATURE:
<223> OTHER INFORMATION: Alpha-1B-glycoprotein peptide

<400> SEQUENCE: 33

Thr Asp Gly Glu Gly Ala Leu Ser Glu Pro Ser Ala Thr Val Thr Ile
1               5                   10                  15

Glu Glu Leu Ala Ala Pro Pro Pro Val Leu Met His His Gly Glu
            20                  25                  30

Ser Ser Gln Val Leu His Pro Gly Asn Lys

```
                          35                  40

<210> SEQ ID NO 34
<211> LENGTH: 8
<212> TYPE: PRT
<213> ORGANISM: Homo sapiens
<220> FEATURE:
<223> OTHER INFORMATION: Alpha-1B-glycoprotein peptide

<400> SEQUENCE: 34

Ser Trp Val Pro His Thr Phe Glu
1               5

<210> SEQ ID NO 35
<211> LENGTH: 10
<212> TYPE: PRT
<213> ORGANISM: Homo sapiens
<220> FEATURE:
<223> OTHER INFORMATION: Alpha-1B-glycoprotein peptide

<400> SEQUENCE: 35

Val Gly Pro Gln His Ala Gly Asn Tyr Arg
1               5                   10

<210> SEQ ID NO 36
<211> LENGTH: 9
<212> TYPE: PRT
<213> ORGANISM: Homo sapiens
<220> FEATURE:
<223> OTHER INFORMATION: Alpha-1B-glycoprotein peptide

<400> SEQUENCE: 36

Ser Thr Gly Trp Thr Gln Leu Ser Lys
1               5

<210> SEQ ID NO 37
<211> LENGTH: 10
<212> TYPE: PRT
<213> ORGANISM: Homo sapiens
<220> FEATURE:
<223> OTHER INFORMATION: Alpha-1B-glycoprotein peptide

<400> SEQUENCE: 37

His Gln Phe Leu Leu Thr Gly Asp Thr Gln
1               5                   10

<210> SEQ ID NO 38
<211> LENGTH: 10
<212> TYPE: PRT
<213> ORGANISM: Homo sapiens
<220> FEATURE:
<223> OTHER INFORMATION: Alpha-1B-glycoprotein peptide

<400> SEQUENCE: 38

Pro Val Ser Trp Ile Thr Pro Gly Leu Lys
1               5                   10

<210> SEQ ID NO 39
<211> LENGTH: 12
<212> TYPE: PRT
<213> ORGANISM: Homo sapiens
<220> FEATURE:
<223> OTHER INFORMATION: Alpha-1B-glycoprotein peptide

<400> SEQUENCE: 39

His Val Asp Gly Pro Pro Arg Pro Gln Leu Arg
1               5                   10
```

```
<210> SEQ ID NO 40
<211> LENGTH: 14
<212> TYPE: PRT
<213> ORGANISM: Homo sapiens
<220> FEATURE:
<223> OTHER INFORMATION: Alpha-1B-glycoprotein peptide

<400> SEQUENCE: 40

Leu Ser Met Ala Pro Val Ser Trp Ile Thr Pro Gly Leu Lys
1               5                   10

<210> SEQ ID NO 41
<211> LENGTH: 15
<212> TYPE: PRT
<213> ORGANISM: Homo sapiens
<220> FEATURE:
<223> OTHER INFORMATION: Alpha-1B-glycoprotein peptide

<400> SEQUENCE: 41

Met His His Gly Glu Ser Ser Gln Val Leu His Pro Gly Asn Lys
1               5                   10                  15

<210> SEQ ID NO 42
<211> LENGTH: 20
<212> TYPE: PRT
<213> ORGANISM: Homo sapiens
<220> FEATURE:
<223> OTHER INFORMATION: Alpha-1B-glycoprotein peptide

<400> SEQUENCE: 42

Ser Gly Leu Ser Thr Gly Trp Thr Gln Leu Ser Lys Leu Leu Glu Leu
1               5                   10                  15

Thr Gly Pro Lys
            20

<210> SEQ ID NO 43
<211> LENGTH: 9
<212> TYPE: PRT
<213> ORGANISM: Homo sapiens
<220> FEATURE:
<223> OTHER INFORMATION: Alpha-1B-glycoprotein peptide

<400> SEQUENCE: 43

Gly Pro Pro Pro Arg Pro Gln Leu Arg
1               5

<210> SEQ ID NO 44
<211> LENGTH: 10
<212> TYPE: PRT
<213> ORGANISM: Homo sapiens
<220> FEATURE:
<223> OTHER INFORMATION: Alpha-1B-glycoprotein peptide

<400> SEQUENCE: 44

Ser Leu Pro Ala Pro Trp Leu Ser Met Ala
1               5                   10

<210> SEQ ID NO 45
<211> LENGTH: 13
<212> TYPE: PRT
<213> ORGANISM: Homo sapiens
<220> FEATURE:
<223> OTHER INFORMATION: Alpha-1B-glycoprotein peptide

<400> SEQUENCE: 45
```

Leu Glu Leu His Val Asp Gly Pro Pro Pro Arg Pro Gln
1               5                   10

<210> SEQ ID NO 46
<211> LENGTH: 15
<212> TYPE: PRT
<213> ORGANISM: Homo sapiens
<220> FEATURE:
<223> OTHER INFORMATION: Alpha-1B-glycoprotein peptide

<400> SEQUENCE: 46

Ile Phe Phe His Leu Asn Ala Val Ala Leu Gly Asp Gly Gly His
1               5                   10                  15

<210> SEQ ID NO 47
<211> LENGTH: 16
<212> TYPE: PRT
<213> ORGANISM: Homo sapiens
<220> FEATURE:
<223> OTHER INFORMATION: Alpha-1B-glycoprotein peptide

<400> SEQUENCE: 47

Asn Gly Val Ala Gln Glu Pro Val His Leu Asp Ser Pro Ala Ile Lys
1               5                   10                  15

<210> SEQ ID NO 48
<211> LENGTH: 20
<212> TYPE: PRT
<213> ORGANISM: Homo sapiens
<220> FEATURE:
<223> OTHER INFORMATION: Alpha-1B-glycoprotein peptide

<400> SEQUENCE: 48

Thr Pro Gly Ala Ala Ala Asn Leu Glu Leu Ile Phe Val Gly Pro Gln
1               5                   10                  15

His Ala Gly Asn
            20

<210> SEQ ID NO 49
<211> LENGTH: 19
<212> TYPE: PRT
<213> ORGANISM: Homo sapiens
<220> FEATURE:
<223> OTHER INFORMATION: Alpha-1B-glycoprotein peptide

<400> SEQUENCE: 49

Leu Pro Ala Pro Trp Leu Ser Met Ala Pro Val Ser Trp Ile Thr Pro
1               5                   10                  15

Gly Leu Lys

<210> SEQ ID NO 50
<211> LENGTH: 6
<212> TYPE: PRT
<213> ORGANISM: Homo sapiens
<220> FEATURE:
<223> OTHER INFORMATION: Alpha-1-acid glycoprotein 1 peptide

<400> SEQUENCE: 50

Thr Tyr Met Leu Ala Phe
1               5

<210> SEQ ID NO 51
<211> LENGTH: 7
<212> TYPE: PRT
<213> ORGANISM: Homo sapiens
<220> FEATURE:

```
<223> OTHER INFORMATION: Alpha-1-acid glycoprotein 1 peptide

<400> SEQUENCE: 51

Ala His Leu Leu Ile Leu Arg
1               5

<210> SEQ ID NO 52
<211> LENGTH: 7
<212> TYPE: PRT
<213> ORGANISM: Homo sapiens
<220> FEATURE:
<223> OTHER INFORMATION: Alpha-1-acid glycoprotein 1 peptide

<400> SEQUENCE: 52

Asn Trp Gly Leu Ser Val Tyr
1               5

<210> SEQ ID NO 53
<211> LENGTH: 7
<212> TYPE: PRT
<213> ORGANISM: Homo sapiens
<220> FEATURE:
<223> OTHER INFORMATION: Alpha-1-acid glycoprotein 1 peptide

<400> SEQUENCE: 53

Thr Tyr Leu Asn Val Gln Arg
1               5

<210> SEQ ID NO 54
<211> LENGTH: 8
<212> TYPE: PRT
<213> ORGANISM: Homo sapiens
<220> FEATURE:
<223> OTHER INFORMATION: Alpha-1-acid glycoprotein 1 peptide

<400> SEQUENCE: 54

Tyr Val Gly Gly Gln Glu His Phe
1               5

<210> SEQ ID NO 55
<211> LENGTH: 8
<212> TYPE: PRT
<213> ORGANISM: Homo sapiens
<220> FEATURE:
<223> OTHER INFORMATION: Alpha-1-acid glycoprotein 1 peptide

<400> SEQUENCE: 55

Phe Ala His Leu Leu Ile Leu Arg
1               5

<210> SEQ ID NO 56
<211> LENGTH: 8
<212> TYPE: PRT
<213> ORGANISM: Homo sapiens
<220> FEATURE:
<223> OTHER INFORMATION: Alpha-1-acid glycoprotein 1 peptide

<400> SEQUENCE: 56

Thr Thr Tyr Leu Asn Val Gln Arg
1               5

<210> SEQ ID NO 57
<211> LENGTH: 9
<212> TYPE: PRT
<213> ORGANISM: Homo sapiens
<220> FEATURE:
<223> OTHER INFORMATION: Alpha-1-acid glycoprotein 1 peptide
```

```
<400> SEQUENCE: 57

Tyr Val Gly Gly Gln Glu His Phe Ala
1               5

<210> SEQ ID NO 58
<211> LENGTH: 10
<212> TYPE: PRT
<213> ORGANISM: Homo sapiens
<220> FEATURE:
<223> OTHER INFORMATION: Alpha-1-acid glycoprotein 1 peptide

<400> SEQUENCE: 58

Tyr Val Gly Gly Gln Glu His Phe Ala His
1               5                   10

<210> SEQ ID NO 59
<211> LENGTH: 10
<212> TYPE: PRT
<213> ORGANISM: Homo sapiens
<220> FEATURE:
<223> OTHER INFORMATION: Alpha-1-acid glycoprotein 1 peptide

<400> SEQUENCE: 59

Glu His Phe Ala His Leu Leu Ile Leu Arg
1               5                   10

<210> SEQ ID NO 60
<211> LENGTH: 9
<212> TYPE: PRT
<213> ORGANISM: Homo sapiens
<220> FEATURE:
<223> OTHER INFORMATION: Alpha-1-acid glycoprotein 1 peptide

<400> SEQUENCE: 60

Ser Asp Val Val Tyr Thr Asp Trp Lys
1               5

<210> SEQ ID NO 61
<211> LENGTH: 11
<212> TYPE: PRT
<213> ORGANISM: Homo sapiens
<220> FEATURE:
<223> OTHER INFORMATION: Alpha-1-acid glycoprotein 1 peptide

<400> SEQUENCE: 61

Tyr Val Gly Gly Gln Glu His Phe Ala His Leu
1               5                   10

<210> SEQ ID NO 62
<211> LENGTH: 10
<212> TYPE: PRT
<213> ORGANISM: Homo sapiens
<220> FEATURE:
<223> OTHER INFORMATION: Alpha-1-acid glycoprotein 1 peptide

<400> SEQUENCE: 62

Met Leu Ala Phe Asp Val Asn Asp Glu Lys
1               5                   10

<210> SEQ ID NO 63
<211> LENGTH: 12
<212> TYPE: PRT
<213> ORGANISM: Homo sapiens
<220> FEATURE:
<223> OTHER INFORMATION: Alpha-1-acid glycoprotein 1 peptide
```

```
<400> SEQUENCE: 63

Tyr Val Gly Gly Gln Glu His Phe Ala His Leu Leu
1               5                   10

<210> SEQ ID NO 64
<211> LENGTH: 12
<212> TYPE: PRT
<213> ORGANISM: Homo sapiens
<220> FEATURE:
<223> OTHER INFORMATION: Alpha-1-acid glycoprotein 1 peptide

<400> SEQUENCE: 64

Gly Gln Glu His Phe Ala His Leu Leu Ile Leu Arg
1               5                   10

<210> SEQ ID NO 65
<211> LENGTH: 11
<212> TYPE: PRT
<213> ORGANISM: Homo sapiens
<220> FEATURE:
<223> OTHER INFORMATION: Alpha-1-acid glycoprotein 1 peptide

<400> SEQUENCE: 65

Ser Val Tyr Ala Asp Lys Pro Glu Thr Thr Lys
1               5                   10

<210> SEQ ID NO 66
<211> LENGTH: 12
<212> TYPE: PRT
<213> ORGANISM: Homo sapiens
<220> FEATURE:
<223> OTHER INFORMATION: Alpha-1-acid glycoprotein 1 peptide

<400> SEQUENCE: 66

Thr Tyr Met Leu Ala Phe Asp Val Asn Asp Glu Lys
1               5                   10

<210> SEQ ID NO 67
<211> LENGTH: 13
<212> TYPE: PRT
<213> ORGANISM: Homo sapiens
<220> FEATURE:
<223> OTHER INFORMATION: Alpha-1-acid glycoprotein 1 peptide

<400> SEQUENCE: 67

Gly Leu Ser Val Tyr Ala Asp Lys Pro Glu Thr Thr Lys
1               5                   10

<210> SEQ ID NO 68
<211> LENGTH: 14
<212> TYPE: PRT
<213> ORGANISM: Homo sapiens
<220> FEATURE:
<223> OTHER INFORMATION: Alpha-1-acid glycoprotein 1 peptide

<400> SEQUENCE: 68

Glu Gln Leu Gly Glu Phe Tyr Glu Ala Leu Asp Cys Leu Arg
1               5                   10

<210> SEQ ID NO 69
<211> LENGTH: 15
<212> TYPE: PRT
<213> ORGANISM: Homo sapiens
<220> FEATURE:
<223> OTHER INFORMATION: Alpha-1-acid glycoprotein 1 peptide

<400> SEQUENCE: 69
```

Tyr Val Gly Gly Gln Glu His Phe Ala His Leu Leu Ile Leu Arg
1               5                   10                  15

<210> SEQ ID NO 70
<211> LENGTH: 14
<212> TYPE: PRT
<213> ORGANISM: Homo sapiens
<220> FEATURE:
<223> OTHER INFORMATION: Alpha-1-acid glycoprotein 1 peptide

<400> SEQUENCE: 70

Trp Gly Leu Ser Val Tyr Ala Asp Lys Pro Glu Thr Thr Lys
1               5                   10

<210> SEQ ID NO 71
<211> LENGTH: 15
<212> TYPE: PRT
<213> ORGANISM: Homo sapiens
<220> FEATURE:
<223> OTHER INFORMATION: Alpha-1-acid glycoprotein 1 peptide

<400> SEQUENCE: 71

Asn Trp Gly Leu Ser Val Tyr Ala Asp Lys Pro Glu Thr Thr Lys
1               5                   10                  15

<210> SEQ ID NO 72
<211> LENGTH: 21
<212> TYPE: PRT
<213> ORGANISM: Homo sapiens
<220> FEATURE:
<223> OTHER INFORMATION: Alpha-1-acid glycoprotein 1 peptide

<400> SEQUENCE: 72

Asp Val Asn Asp Glu Lys Asn Trp Gly Leu Ser Val Tyr Ala Asp Lys
1               5                   10                  15

Pro Glu Thr Thr Lys
            20

<210> SEQ ID NO 73
<211> LENGTH: 27
<212> TYPE: PRT
<213> ORGANISM: Homo sapiens
<220> FEATURE:
<223> OTHER INFORMATION: Alpha-1-acid glycoprotein 1 peptide

<400> SEQUENCE: 73

Thr Tyr Met Leu Ala Phe Asp Val Asn Asp Glu Lys Asn Trp Gly Leu
1               5                   10                  15

Ser Val Tyr Ala Asp Lys Pro Glu Thr Thr Lys
            20                  25

<210> SEQ ID NO 74
<211> LENGTH: 7
<212> TYPE: PRT
<213> ORGANISM: Homo sapiens
<220> FEATURE:
<223> OTHER INFORMATION: Alpha-1-acid glycoprotein 1 peptide

<400> SEQUENCE: 74

Val Val Tyr Thr Asp Trp Lys
1               5

<210> SEQ ID NO 75
<211> LENGTH: 10
<212> TYPE: PRT

```
<213> ORGANISM: Homo sapiens
<220> FEATURE:
<223> OTHER INFORMATION: >Alpha-1-acid glycoprotein 1 peptide

<400> SEQUENCE: 75

Val Tyr Ala Asp Lys Pro Glu Thr Thr Lys
1               5                   10

<210> SEQ ID NO 76
<211> LENGTH: 14
<212> TYPE: PRT
<213> ORGANISM: Homo sapiens
<220> FEATURE:
<223> OTHER INFORMATION: Alpha-1-acid glycoprotein 1 peptide

<400> SEQUENCE: 76

Val Gly Gly Gln Glu His Phe Ala His Leu Leu Ile Leu Arg
1               5                   10

<210> SEQ ID NO 77
<211> LENGTH: 12
<212> TYPE: PRT
<213> ORGANISM: Homo sapiens
<220> FEATURE:
<223> OTHER INFORMATION: Alpha-1-acid glycoprotein 1 peptide

<400> SEQUENCE: 77

Ile Pro Lys Ser Asp Val Val Tyr Thr Asp Trp Lys
1               5                   10

<210> SEQ ID NO 78
<211> LENGTH: 13
<212> TYPE: PRT
<213> ORGANISM: Homo sapiens
<220> FEATURE:
<223> OTHER INFORMATION: Alpha-1-acid glycoprotein 1 peptide

<400> SEQUENCE: 78

Gly Gly Gln Glu His Phe Ala His Leu Leu Ile Leu Arg
1               5                   10

<210> SEQ ID NO 79
<211> LENGTH: 7
<212> TYPE: PRT
<213> ORGANISM: Homo sapiens
<220> FEATURE:
<223> OTHER INFORMATION: Ig lambda-2 chain C regions

<400> SEQUENCE: 79

Ala Asp Ser Ser Pro Val Lys
1               5

<210> SEQ ID NO 80
<211> LENGTH: 9
<212> TYPE: PRT
<213> ORGANISM: Homo sapiens
<220> FEATURE:
<223> OTHER INFORMATION: Ig lambda-2 chain C regions

<400> SEQUENCE: 80

Gly Val Glu Thr Thr Thr Pro Ser Lys
1               5

<210> SEQ ID NO 81
<211> LENGTH: 10
<212> TYPE: PRT
<213> ORGANISM: Homo sapiens
```

```
<220> FEATURE:
<223> OTHER INFORMATION: Ig lambda-2 chain C regions

<400> SEQUENCE: 81

Ala Gly Val Glu Thr Thr Thr Pro Ser Lys
1               5                   10

<210> SEQ ID NO 82
<211> LENGTH: 11
<212> TYPE: PRT
<213> ORGANISM: Homo sapiens
<220> FEATURE:
<223> OTHER INFORMATION: Ig lambda-2 chain C regions

<400> SEQUENCE: 82

Lys Ala Gly Val Glu Thr Thr Thr Pro Ser Lys
1               5                   10

<210> SEQ ID NO 83
<211> LENGTH: 6
<212> TYPE: PRT
<213> ORGANISM: Homo sapiens
<220> FEATURE:
<223> OTHER INFORMATION: Serotransferrin peptide

<400> SEQUENCE: 83

Val Tyr Ile Ala Gly Lys
1               5

<210> SEQ ID NO 84
<211> LENGTH: 7
<212> TYPE: PRT
<213> ORGANISM: Homo sapiens
<220> FEATURE:
<223> OTHER INFORMATION: Serotransferrin peptide

<400> SEQUENCE: 84

Asp Ser Gly Phe Gln Met Asn
1               5

<210> SEQ ID NO 85
<211> LENGTH: 7
<212> TYPE: PRT
<213> ORGANISM: Homo sapiens
<220> FEATURE:
<223> OTHER INFORMATION: Serotransferrin peptide

<400> SEQUENCE: 85

His Ser Thr Ile Phe Glu Asn
1               5

<210> SEQ ID NO 86
<211> LENGTH: 6
<212> TYPE: PRT
<213> ORGANISM: Homo sapiens
<220> FEATURE:
<223> OTHER INFORMATION: Serotransferrin peptide

<400> SEQUENCE: 86

Gly Leu Leu Tyr Asn Lys
1               5

<210> SEQ ID NO 87
<211> LENGTH: 8
<212> TYPE: PRT
<213> ORGANISM: Homo sapiens
<220> FEATURE:
```

```
<223> OTHER INFORMATION: Serotransferrin peptide

<400> SEQUENCE: 87

Ser Ala Gly Trp Asn Ile Pro Ile
1               5

<210> SEQ ID NO 88
<211> LENGTH: 6
<212> TYPE: PRT
<213> ORGANISM: Homo sapiens
<220> FEATURE:
<223> OTHER INFORMATION: Serotransferrin peptide

<400> SEQUENCE: 88

Pro Asp Pro Trp Ala Lys
1               5

<210> SEQ ID NO 89
<211> LENGTH: 7
<212> TYPE: PRT
<213> ORGANISM: Homo sapiens
<220> FEATURE:
<223> OTHER INFORMATION: Serotransferrin peptide

<400> SEQUENCE: 89

Met Tyr Leu Gly Tyr Glu Tyr
1               5

<210> SEQ ID NO 90
<211> LENGTH: 7
<212> TYPE: PRT
<213> ORGANISM: Homo sapiens
<220> FEATURE:
<223> OTHER INFORMATION: Serotransferrin peptide

<400> SEQUENCE: 90

Asn Pro Asp Pro Trp Ala Lys
1               5

<210> SEQ ID NO 91
<211> LENGTH: 8
<212> TYPE: PRT
<213> ORGANISM: Homo sapiens
<220> FEATURE:
<223> OTHER INFORMATION: Serotransferrin peptide

<400> SEQUENCE: 91

Asp Ser Ala His Gly Phe Leu Lys
1               5

<210> SEQ ID NO 92
<211> LENGTH: 8
<212> TYPE: PRT
<213> ORGANISM: Homo sapiens
<220> FEATURE:
<223> OTHER INFORMATION: Serotransferrin peptide

<400> SEQUENCE: 92

Phe Gly Tyr Ser Gly Ala Phe Lys
1               5

<210> SEQ ID NO 93
<211> LENGTH: 8
<212> TYPE: PRT
<213> ORGANISM: Homo sapiens
<220> FEATURE:
<223> OTHER INFORMATION: Serotransferrin peptide
```

```
<400> SEQUENCE: 93

Val Ala Glu Phe Tyr Gly Ser Lys
1               5

<210> SEQ ID NO 94
<211> LENGTH: 8
<212> TYPE: PRT
<213> ORGANISM: Homo sapiens
<220> FEATURE:
<223> OTHER INFORMATION: Serotransferrin peptide

<400> SEQUENCE: 94

Lys Asp Ser Gly Phe Gln Met Asn
1               5

<210> SEQ ID NO 95
<211> LENGTH: 9
<212> TYPE: PRT
<213> ORGANISM: Homo sapiens
<220> FEATURE:
<223> OTHER INFORMATION: Serotransferrin peptide

<400> SEQUENCE: 95

Glu Phe Gln Leu Phe Ser Ser Pro His
1               5

<210> SEQ ID NO 96
<211> LENGTH: 8
<212> TYPE: PRT
<213> ORGANISM: Homo sapiens
<220> FEATURE:
<223> OTHER INFORMATION: Serotransferrin peptide

<400> SEQUENCE: 96

Lys Pro Val Glu Glu Tyr Ala Asn
1               5

<210> SEQ ID NO 97
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 97

Asp Gly Ala Gly Asp Val Ala Phe Val Lys
1               5                   10

<210> SEQ ID NO 98
<211> LENGTH: 11
<212> TYPE: PRT
<213> ORGANISM: Homo sapiens
<220> FEATURE:
<223> OTHER INFORMATION: Serotransferrin peptide

<400> SEQUENCE: 98

Ser Ala Gly Trp Asn Ile Pro Ile Gly Leu Leu
1               5                   10

<210> SEQ ID NO 99
<211> LENGTH: 9
<212> TYPE: PRT
<213> ORGANISM: Homo sapiens
<220> FEATURE:
<223> OTHER INFORMATION: Serotransferrin peptide
```

```
<400> SEQUENCE: 99

Glu Asp Leu Ile Trp Glu Leu Leu Asn
 1               5

<210> SEQ ID NO 100
<211> LENGTH: 8
<212> TYPE: PRT
<213> ORGANISM: Homo sapiens
<220> FEATURE:
<223> OTHER INFORMATION: Serotransferrin peptide

<400> SEQUENCE: 100

Tyr Leu Gly Glu Glu Tyr Val Lys
 1               5

<210> SEQ ID NO 101
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 101

His Ser Thr Ile Phe Glu Asn Leu Ala Asn
 1               5                  10

<210> SEQ ID NO 102
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 102

Gly Tyr Tyr Gly Tyr Thr Gly Ala Phe Arg
 1               5                  10

<210> SEQ ID NO 103
<211> LENGTH: 7
<212> TYPE: PRT
<213> ORGANISM: Homo sapiens
<220> FEATURE:
<223> OTHER INFORMATION: Serotransferrin peptide

<400> SEQUENCE: 103

Lys Pro Val Asp Glu Tyr Lys
 1               5

<210> SEQ ID NO 104
<211> LENGTH: 9
<212> TYPE: PRT
<213> ORGANISM: Homo sapiens
<220> FEATURE:
<223> OTHER INFORMATION: Serotransferrin peptide

<400> SEQUENCE: 104

Ile Pro Met Gly Leu Leu Tyr Asn Lys
 1               5

<210> SEQ ID NO 105
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 105
```

```
Asp Ser Gly Phe Gln Met Asn Gln Leu Arg
1               5                   10

<210> SEQ ID NO 106
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 106

Pro Val Val Ala Glu Phe Tyr Gly Ser Lys
1               5                   10

<210> SEQ ID NO 107
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 107

Leu Ala Gln Val Pro Ser His Thr Val Val Ala Arg
1               5                   10

<210> SEQ ID NO 108
<211> LENGTH: 8
<212> TYPE: PRT
<213> ORGANISM: Homo sapiens
<220> FEATURE:
<223> OTHER INFORMATION: Serotransferrin peptide

<400> SEQUENCE: 108

Lys Pro Val Asp Glu Tyr Lys Asp
1               5

<210> SEQ ID NO 109
<211> LENGTH: 11
<212> TYPE: PRT
<213> ORGANISM: Homo sapiens
<220> FEATURE:
<223> OTHER INFORMATION: Serotransferrin peptide

<400> SEQUENCE: 109

Glu Gly Tyr Tyr Gly Tyr Thr Gly Ala Phe Arg
1               5                   10

<210> SEQ ID NO 110
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 110

Ser Ala Gly Trp Asn Ile Pro Ile Gly Leu Leu Tyr
1               5                   10

<210> SEQ ID NO 111
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 111
```

```
Asn Ile Pro Met Gly Leu Leu Tyr Asn Lys
1               5                   10
```

<210> SEQ ID NO 112
<211> LENGTH: 11
<212> TYPE: PRT
<213> ORGANISM: Homo sapiens
<220> FEATURE:
<223> OTHER INFORMATION: Serotransferrin peptide

<400> SEQUENCE: 112

```
His Gln Thr Val Pro Gln Asn Thr Gly Gly Lys
1               5                   10
```

<210> SEQ ID NO 113
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 113

```
Gln Tyr Phe Gly Tyr Ser Gly Ala Phe Lys
1               5                   10
```

<210> SEQ ID NO 114
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 114

```
Thr Ala Gly Trp Asn Ile Pro Met Gly Leu Leu Tyr
1               5                   10
```

<210> SEQ ID NO 115
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 115

```
Ser Leu Asp Gly Gly Phe Val Tyr Ile Ala Gly Lys
1               5                   10
```

<210> SEQ ID NO 116
<211> LENGTH: 11
<212> TYPE: PRT
<213> ORGANISM: Homo sapiens
<220> FEATURE:
<223> OTHER INFORMATION: Serotransferrin peptide

<400> SEQUENCE: 116

```
Ser Ala Ser Asp Leu Thr Trp Asp Asn Leu Lys
1               5                   10
```

<210> SEQ ID NO 117
<211> LENGTH: 11
<212> TYPE: PRT
<213> ORGANISM: Homo sapiens
<220> FEATURE:
<223> OTHER INFORMATION: Serotransferrin peptide

<400> SEQUENCE: 117

```
His Ser Thr Ile Phe Glu Asn Leu Ala Asn Lys
```

```
1               5                   10
```

<210> SEQ ID NO 118
<211> LENGTH: 11
<212> TYPE: PRT
<213> ORGANISM: Homo sapiens
<220> FEATURE:
<223> OTHER INFORMATION: Serotransferrin peptide

<400> SEQUENCE: 118

```
Glu Phe Gln Leu Phe Ser Ser Pro His Gly Lys
1               5                   10
```

<210> SEQ ID NO 119
<211> LENGTH: 13
<212> TYPE: PRT
<213> ORGANISM: Homo sapiens
<220> FEATURE:
<223> OTHER INFORMATION: Serotransferrin peptide

<400> SEQUENCE: 119

```
Thr Ala Gly Trp Asn Ile Pro Met Gly Leu Leu Tyr Asn
1               5                   10
```

<210> SEQ ID NO 120
<211> LENGTH: 11
<212> TYPE: PRT
<213> ORGANISM: Homo sapiens
<220> FEATURE:
<223> OTHER INFORMATION: Serotransferrin peptide

<400> SEQUENCE: 120

```
Ser Lys Glu Phe Gln Leu Phe Ser Ser Pro His
1               5                   10
```

<210> SEQ ID NO 121
<211> LENGTH: 11
<212> TYPE: PRT
<213> ORGANISM: Homo sapiens
<220> FEATURE:
<223> OTHER INFORMATION: Serotransferrin peptide

<400> SEQUENCE: 121

```
Lys Asp Ser Gly Phe Gln Met Asn Gln Leu Arg
1               5                   10
```

<210> SEQ ID NO 122
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 122

```
Glu Asp Leu Ile Trp Glu Leu Leu Asn Gln Ala Gln
1               5                   10
```

<210> SEQ ID NO 123
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 123

```
Met Tyr Leu Gly Tyr Glu Tyr Val Thr Ala Ile Arg
1               5                   10
```

```
<210> SEQ ID NO 124
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 124

Lys Glu Gly Tyr Tyr Gly Tyr Thr Gly Ala Phe Arg
1               5                   10

<210> SEQ ID NO 125
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 125

Leu Lys Pro Val Val Ala Glu Phe Tyr Gly Ser Lys
1               5                   10

<210> SEQ ID NO 126
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 126

Lys Ser Ala Ser Asp Leu Thr Trp Asp Asn Leu Lys
1               5                   10

<210> SEQ ID NO 127
<211> LENGTH: 14
<212> TYPE: PRT
<213> ORGANISM: Homo sapiens
<220> FEATURE:
<223> OTHER INFORMATION: Serotransferrin peptide

<400> SEQUENCE: 127

Thr Ala Gly Trp Asn Ile Pro Met Gly Leu Leu Tyr Asn Lys
1               5                   10

<210> SEQ ID NO 128
<211> LENGTH: 14
<212> TYPE: PRT
<213> ORGANISM: Homo sapiens
<220> FEATURE:
<223> OTHER INFORMATION: Serotransferrin peptide

<400> SEQUENCE: 128

Ser Thr Leu Asn Gln Tyr Phe Gly Tyr Ser Gly Ala Phe Lys
1               5                   10

<210> SEQ ID NO 129
<211> LENGTH: 13
<212> TYPE: PRT
<213> ORGANISM: Homo sapiens
<220> FEATURE:
<223> OTHER INFORMATION: Serotransferrin peptide

<400> SEQUENCE: 129

Asn Leu Lys Pro Val Val Ala Glu Phe Tyr Gly Ser Lys
1               5                   10
```

```
<210> SEQ ID NO 130
<211> LENGTH: 14
<212> TYPE: PRT
<213> ORGANISM: Homo sapiens
<220> FEATURE:
<223> OTHER INFORMATION: Serotransferrin peptide

<400> SEQUENCE: 130

Glu Asp Pro Gln Thr Phe Tyr Tyr Ala Val Ala Val Val Lys
1               5                   10

<210> SEQ ID NO 131
<211> LENGTH: 13
<212> TYPE: PRT
<213> ORGANISM: Homo sapiens
<220> FEATURE:
<223> OTHER INFORMATION: Serotransferrin peptide

<400> SEQUENCE: 131

Ser Lys Glu Phe Gln Leu Phe Ser Ser Pro His Gly Lys
1               5                   10

<210> SEQ ID NO 132
<211> LENGTH: 21
<212> TYPE: PRT
<213> ORGANISM: Homo sapiens
<220> FEATURE:
<223> OTHER INFORMATION: Serotransferrin peptide

<400> SEQUENCE: 132

Ala Ile Ala Ala Asn Glu Ala Asp Ala Val Thr Leu Asp Ala Gly Leu
1               5                   10                  15

Val Tyr Asp Ala Tyr
            20

<210> SEQ ID NO 133
<211> LENGTH: 17
<212> TYPE: PRT
<213> ORGANISM: Homo sapiens
<220> FEATURE:
<223> OTHER INFORMATION: Serotransferrin peptide

<400> SEQUENCE: 133

Leu Ala Pro Asn Asn Leu Lys Pro Val Val Ala Glu Phe Tyr Gly Ser
1               5                   10                  15

Lys

<210> SEQ ID NO 134
<211> LENGTH: 17
<212> TYPE: PRT
<213> ORGANISM: Homo sapiens
<220> FEATURE:
<223> OTHER INFORMATION: Serotransferrin peptide

<400> SEQUENCE: 134

Glu Asp Leu Ile Trp Glu Leu Leu Asn Gln Ala Gln Glu His Phe Gly
1               5                   10                  15

Lys

<210> SEQ ID NO 135
<211> LENGTH: 21
<212> TYPE: PRT
<213> ORGANISM: Homo sapiens
<220> FEATURE:
<223> OTHER INFORMATION: Serotransferrin peptide
```

```
<400> SEQUENCE: 135

Ile Met Asn Gly Glu Ala Asp Ala Met Ser Leu Asp Gly Gly Phe Val
1               5                   10                  15

Tyr Ile Ala Gly Lys
            20

<210> SEQ ID NO 136
<211> LENGTH: 25
<212> TYPE: PRT
<213> ORGANISM: Homo sapiens
<220> FEATURE:
<223> OTHER INFORMATION: Serotransferrin peptide

<400> SEQUENCE: 136

Ala Ile Ala Ala Asn Glu Ala Asp Ala Val Thr Leu Asp Ala Gly Leu
1               5                   10                  15

Val Tyr Asp Ala Tyr Leu Ala Pro Asn
            20                  25

<210> SEQ ID NO 137
<211> LENGTH: 19
<212> TYPE: PRT
<213> ORGANISM: Homo sapiens
<220> FEATURE:
<223> OTHER INFORMATION: Serotransferrin peptide

<400> SEQUENCE: 137

Gly Lys Glu Asp Leu Ile Trp Glu Leu Leu Asn Gln Ala Gln Glu His
1               5                   10                  15

Phe Gly Lys

<210> SEQ ID NO 138
<211> LENGTH: 20
<212> TYPE: PRT
<213> ORGANISM: Homo sapiens
<220> FEATURE:
<223> OTHER INFORMATION: Serotransferrin peptide

<400> SEQUENCE: 138

Gly Gly Lys Glu Asp Leu Ile Trp Glu Leu Leu Asn Gln Ala Gln Glu
1               5                   10                  15

His Phe Gly Lys
            20

<210> SEQ ID NO 139
<211> LENGTH: 19
<212> TYPE: PRT
<213> ORGANISM: Homo sapiens
<220> FEATURE:
<223> OTHER INFORMATION: Serotransferrin peptide

<400> SEQUENCE: 139

Glu Asp Leu Ile Trp Glu Leu Leu Asn Gln Ala Gln Glu His Phe Gly
1               5                   10                  15

Lys Asp Lys

<210> SEQ ID NO 140
<211> LENGTH: 22
<212> TYPE: PRT
<213> ORGANISM: Homo sapiens
<220> FEATURE:
<223> OTHER INFORMATION: Serotransferrin peptide
```

<400> SEQUENCE: 140

Ser Met Gly Gly Lys Glu Asp Leu Ile Trp Glu Leu Leu Asn Gln Ala
1               5                   10                  15

Gln Glu His Phe Gly Lys
            20

<210> SEQ ID NO 141
<211> LENGTH: 38
<212> TYPE: PRT
<213> ORGANISM: Homo sapiens
<220> FEATURE:
<223> OTHER INFORMATION: Serotransferrin peptide

<400> SEQUENCE: 141

Ala Ile Ala Ala Asn Glu Ala Asp Ala Val Thr Leu Asp Ala Gly Leu
1               5                   10                  15

Val Tyr Asp Ala Tyr Leu Ala Pro Asn Asn Leu Lys Pro Val Val Ala
            20                  25                  30

Glu Phe Tyr Gly Ser Lys
            35

<210> SEQ ID NO 142
<211> LENGTH: 8
<212> TYPE: PRT
<213> ORGANISM: Homo sapiens
<220> FEATURE:
<223> OTHER INFORMATION: Serotransferrin peptide

<400> SEQUENCE: 142

Ala Pro Asn His Ala Val Val Thr
1               5

<210> SEQ ID NO 143
<211> LENGTH: 9
<212> TYPE: PRT
<213> ORGANISM: Homo sapiens
<220> FEATURE:
<223> OTHER INFORMATION: Serotransferrin peptide

<400> SEQUENCE: 143

Ala Pro Asn His Ala Val Val Thr Arg
1               5

<210> SEQ ID NO 144
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 144

Ser Ala Gly Trp Asn Ile Pro Ile Gly Leu
1               5                   10

<210> SEQ ID NO 145
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 145

Gln Val Pro Ser His Thr Val Val Ala Arg
1               5                   10

<210> SEQ ID NO 146
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 146

Ser Thr Ile Phe Glu Asn Leu Ala Asn Lys
1               5                   10

<210> SEQ ID NO 147
<211> LENGTH: 13
<212> TYPE: PRT
<213> ORGANISM: Homo sapiens
<220> FEATURE:
<223> OTHER INFORMATION: Serotransferrin peptide

<400> SEQUENCE: 147

His Leu Ala Gln Val Pro Ser His Thr Val Val Ala Arg
1               5                   10

<210> SEQ ID NO 148
<211> LENGTH: 12
<212> TYPE: PRT
<213> ORGANISM: Homo sapiens
<220> FEATURE:
<223> OTHER INFORMATION: Serotransferrin peptide

<400> SEQUENCE: 148

Gly Trp Asn Ile Pro Met Gly Leu Leu Tyr Asn Lys
1               5                   10

<210> SEQ ID NO 149
<211> LENGTH: 15
<212> TYPE: PRT
<213> ORGANISM: Homo sapiens
<220> FEATURE:
<223> OTHER INFORMATION: Serotransferrin peptide

<400> SEQUENCE: 149

Met Tyr Leu Gly Tyr Glu Tyr Val Thr Ala Ile Arg Asn Leu Arg
1               5                   10                  15

<210> SEQ ID NO 150
<211> LENGTH: 15
<212> TYPE: PRT
<213> ORGANISM: Homo sapiens
<220> FEATURE:
<223> OTHER INFORMATION: Serotransferrin peptide

<400> SEQUENCE: 150

Pro Asn Asn Leu Lys Pro Val Val Ala Glu Phe Tyr Gly Ser Lys
1               5                   10                  15

<210> SEQ ID NO 151
<211> LENGTH: 9
<212> TYPE: PRT
<213> ORGANISM: Homo sapiens
<220> FEATURE:
<223> OTHER INFORMATION: Serotransferrin peptide

<400> SEQUENCE: 151

His Ser Thr Ile Phe Glu Asn Leu Ala
1               5

```
<210> SEQ ID NO 152
<211> LENGTH: 9
<212> TYPE: PRT
<213> ORGANISM: Homo sapiens
<220> FEATURE:
<223> OTHER INFORMATION: Serotransferrin peptide

<400> SEQUENCE: 152

Ala Asp Arg Asp Gln Tyr Glu Leu Leu
1               5

<210> SEQ ID NO 153
<211> LENGTH: 9
<212> TYPE: PRT
<213> ORGANISM: Homo sapiens
<220> FEATURE:
<223> OTHER INFORMATION: Serotransferrin peptide

<400> SEQUENCE: 153

Gln Leu Phe Ser Ser Pro His Gly Lys
1               5

<210> SEQ ID NO 154
<211> LENGTH: 10
<212> TYPE: PRT
<213> ORGANISM: Homo sapiens
<220> FEATURE:
<223> OTHER INFORMATION: Serotransferrin peptide

<400> SEQUENCE: 154

Leu Gly Tyr Glu Tyr Val Thr Ala Ile Arg
1               5                   10

<210> SEQ ID NO 155
<211> LENGTH: 14
<212> TYPE: PRT
<213> ORGANISM: Homo sapiens
<220> FEATURE:
<223> OTHER INFORMATION: Serotransferrin peptide

<400> SEQUENCE: 155

His Ser Thr Ile Phe Glu Asn Leu Ala Asn Lys Ala Asp Arg
1               5                   10

<210> SEQ ID NO 156
<211> LENGTH: 18
<212> TYPE: PRT
<213> ORGANISM: Homo sapiens
<220> FEATURE:
<223> OTHER INFORMATION: Serotransferrin peptide

<400> SEQUENCE: 156

His Gln Thr Val Pro Gln Asn Thr Gly Gly Lys Asn Pro Asp Pro Trp
1               5                   10                  15

Ala Lys

<210> SEQ ID NO 157
<211> LENGTH: 18
<212> TYPE: PRT
<213> ORGANISM: Homo sapiens
<220> FEATURE:
<223> OTHER INFORMATION: Serotransferrin peptide

<400> SEQUENCE: 157

Lys Glu Asp Leu Ile Trp Glu Leu Leu Asn Gln Ala Gln Glu His Phe
1               5                   10                  15
```

```
Gly Lys

<210> SEQ ID NO 158
<211> LENGTH: 24
<212> TYPE: PRT
<213> ORGANISM: Homo sapiens
<220> FEATURE:
<223> OTHER INFORMATION: Serotransferrin peptide

<400> SEQUENCE: 158

Gly Leu Val Tyr Asp Ala Tyr Leu Ala Pro Asn Asn Leu Lys Pro Val
1               5                   10                  15

Val Ala Glu Phe Tyr Gly Ser Lys
            20
```

METHODS FOR DIAGNOSIS, DIFFERENTIATION AND MONITORING USING URINE PROTEINS AS MARKERS IN IGA NEPHROPATHY

The Sequence Listing in ASCII text file format of 34,922 bytes in size, created on Dec. 18, 2018, with the file name "2018-12-21SequenceListing_MUCHA1," filed in the U.S. Patent and Trademark Office on even date herewith, is hereby incorporated herein by reference.

TECHNICAL FIELD

The application relates the field of diagnostic methods of IgA nephropathy. The present invention is directed to methods for diagnosis, differentiation and monitoring using urine proteins as markers in IgA nephropathy. In addition corresponding diagnostic kits are provided.

BACKGROUND OF THE INVENTION

IgA nephropathy (IgAN) is the most common primary glomerulonephritis worldwide that may lead to a chronic kidney disease (CKD). CKD represents an increasing worldwide public health problem, which causes an extensive socio-economic burden for the society. The prevalence of CKD is up to 14.2% in the USA, 10.2% in Norway, and 11.9% in Poland. It is estimated that over 4 million people in Poland suffer from CKD and the number of patients with end stage renal disease (ESRD) on dialysis in Poland exceeds 18 000, in addition to 13 300 renal transplant recipients. Both, early stages of CKD and ESRD are associated with high morbidity and increased healthcare utilization. For example, in England, according to a recent report published by NHS Kidney Care, chronic kidney disease costs more than breast, lung, colon and skin cancer combined. Therefore, the IgAN focuses attention of researchers, clinicians and healthcare providers. The individuals affected by IgAN develop characteristic IgA-containing antibody complexes that deposit in the kidney producing tissue injury. Up to date, kidney biopsy with histopathologic evaluation is the best available method to diagnose IgAN. IgAN is a genetically complex trait, and not much is known about its pathogenesis and pathophysiology. Therefore, the treatment options are presently limited and empirics-based.

It is hoped that with an early diagnosis and treatment, it's possible to slow or even halt the progression of kidney diseases, such as IgAN. A pressing need also exists for personalizing the medical care and finding new molecularly targeted therapies in this disease. A great potential for new findings regarding diagnostic procedures for kidney disease lies in the '-omics' technologies, which can provide new data in regard to IgAN biology. Notably, however, while genetics-based methods can provide information correlated with the pathogenesis of the disease, the most directly related to its pathophysiology are the expression and production of proteins. The most accurate screening information as to the presence of specific proteins provides proteomics. Therefore, one of the most promising diagnostic tools is urine proteomics, particularly because the biological material can be obtained easily and comes directly from the diseased organ, the kidney. Indeed, it was previously reported that the presence of urinary proteins is indicative of glomerular damage and interstitial fibrosis. During the last decade, several valuable studies have linked proteomics to IgAN, and a number of urine proteins considered IgAN-specific have been reported. The study published by Mucha K at al. (Pol Arch Med Wewn. 2014; 124:380-6) presents a systematic analysis of urine proteomics from renal disease patients, namely IgAN versus healthy controls. Notably, the discoveries of alpha-1B-glycoprotein (A1BG), alpha-1-acid glycoprotein 1 (ORM1), Ig lambda-2 chain C regions (IGLC2) and serotransferrin (TF) have not been disclosed in Mucha et al.

Methods for kidney disease detection by protein profiling are known in the prior art. For example, WO2003002757 (A1) relates to improved methods of detecting an early stage of renal disease and/or renal complications of a disease, particularly diabetes, and discloses a1 acid glycoprotein (also known as orosomucoid) that is used in a method for diagnosing a renal disease and/or renal complications of a disease in a subject. The disease comprises a disease selected from the group consisting of diabetes insipidus, diabetes type I, diabetes II and renal disease, including IgA nephropathy. The invention provides a method of generating and analysis a urinary protein fragmentation profile, in terms of the size, and sequence of particular fragments derived from intact filtered proteins together with the position where enzymes scission occurs along the protein polypeptide chain is characteristic of the diseased state of the kidney.

US20160061845 (A1) discloses a method of diagnosing and treating a subject having a nephrotic syndrome, comprising the step of determining the level of one or more biomarkers in a biofluid, wherein the biomarker indicates a level of a protein selected from Vitamin D-binding protein (VDBP), Neutrophil gelatinase-associated lipocalin (NGAL), Fetuin A, AGP1, AGP2, A2MCG, and prealbumin.

U.S. Pat. No. 8,927,220 (B2) relates to the development of a protein that can be used for diagnosing IgA nephropathy and thin-glomerular-basement-membrane (hereinafter, referred to as "TGBM") nephropathy, and used as a biomarker for diagnosing serious cases thereof, and more particularly to a biomarker protein that shows increased/decreased levels in urine of IgA nephropathy patients or TGBM nephropathy patients compared to those in urine of normal people, and a diagnostic kit using the biomarker protein, which can be used to diagnose IgA nephropathy and TGBM nephropathy early, and predict and determine the degree of progression of the disease in advance. The biomarker protein that shows increased/decreased levels in urine of IgA nephropathy patients or TGBM nephropathy patients is selected from a vast list of biomarkers including Ceruloplasmin precursor, Alpha-1-antitrypsin precursor, Serotransferrin precursor Transferrin variant Fragment and Alpha-2-macroglobulin precursor.

US20140038203 (A1) discloses a method of detecting or predicting the onset or magnitude of kidney disease, such as acute kidney disease (AKI), previously called acute renal failure 1ARF. In various aspects, methods and kits are provided to detect specific urinary proteins associated with AKI diagnosis or prognosis using (a) angiotensinogen, apolipoprotein A-IV, pigment epithelium-derived factor, thymosin J34, insulin-like growth factor-binding protein I, myoglobin, vitamin D binding protein, complement C4-B, profilin-1, alpha-i antitrypsin, fibrinogen alpha chain, glutathione peroxidase 3, superoxide dismutase [Cu Zn], complement C3, antithrombin neutrophil defensin 1, and (b) non-secretory ribonuclease, secreted Ly-6/uPAR-related protein I, pro-epidermal growth factor precursor (pro-EGF protein), and CD59 glycoprotein. Also the following markers are disclosed: Serotransferrin (P02787), Alpha-1-acid glycoprotein 1 (P02763), Alpha-1-acid glycoprotein 2 (ORM2) (P19652), Alpha-IB-glycoprotein (P04217), Ig lambda-2 chain C regions (IGLC2) (POCG05), Platelet glycoprotein VI (GP6) (Q9HCN6), SERPINA1, SERPINA3, SERPINA5, SERPINA7 and Cytosolic non-specific dipeptidase (CNDP2).

WO2013152989 (A2) relates to a cancer diagnostic and/or therapeutic and/or prognostic and/or patient stratification biomarker assay for the prognosis and/or diagnosis and/or therapy of colorectal cancer and/or lung cancer and/or pancreatic cancer comprising the combined measurement of at least two, preferably at least three protein/peptide biomarkers and/or fragments of protein biomarkers selected from a first group consisting of: CP; SERPINA3; PON1; optionally in combination with at least one or both protein/peptide biomarkers and/or fragments of protein biomarkers selected from a second group consisting of: IGFBP3; ATRN; LR61; TIMP1. In this publication SERPINA6 marker is also disclosed.

WO2011035323 (A1) relates to methods and compositions for monitoring, diagnosis, prognosis, and determination of treatment regimens in subjects suffering from or suspected of having a renal injury. In particular, the invention relates to using a plurality of assays, one or more of which is configured to detect a kidney injury marker as diagnostic and prognostic biomarkers in renal injuries. Additional clinical indicia may be combined with the kidney injury marker assay result(s) of the present invention. These include other biomarkers related to renal status. Examples include the following consisting of metalloproteinase inhibitor 2, soluble oxidized low-density lipoprotein receptor 1, interleukin-2, von Willebrand factor, granulocyte-macrophage colony-stimulating factor, tumor necrosis factor receptor superfamily member 11B, neutrophil elastase, interleukin-1 beta, heart-type fatty acid-binding protein, beta-2-glycoprotein 1, soluble CD40 ligand, coagulation factor VII, C-C motif chemokine 2, IgM, CA 19-9, IL-10, TNF-01, and myoglobin. It also discloses Ferritin (light chain, P02793; heavy chain P02794) and Alpha-1-acid glycoprotein 1 (P02763).

US2014235503 A1 indicates CNDP1 (also known as carnosinase) as protein associated with kidney function/dysfunction and publication in Postepy Hig. Med. Dosw. (2012); vol. 66, pages 215-221 discloses results of studies concerning carnosinase's role in kidney diseases, particularly in ischemia/reperfusion induced acute renal failure, diabetic nephropathy, gentamicin-induced nephrotoxicity and also in blood pressure regulation.

Even though a number of different markers related to renal diseases is significant, there still exists a need for providing highly selective and sensitive diagnostic methods and tests that would enable diagnosis and monitoring of IgAN. Moreover, there is a need for methods that are suitable to differentiate IgAN from other chronic kidney diseases.

DISCLOSURE OF INVENTION

The present invention aims to solve the above identified problems. The present inventors have disclosed that the urine protein concentration of alpha-1B-glycoprotein (A1BG), alpha-1-acid glycoprotein 1 (ORM1), Ig lambda-2 chain C regions (IGLC2), and serotransferrin (TF) level is changed in urine samples collected from patients suffering from IgA nephropathy (IgAN), as compared to healthy individuals or individuals with renal diseases of a different etiology, in particular autosomal dominant polycystic kidney disease (ADPKD) and lupus nephritis (LN). In particular, the expression of said markers in IgAN patients is higher than in healthy individuals or individuals with renal diseases of other etiology, such as ADPKD and LN. The term "expression" as used herein corresponds to amounts of said markers or their concentration levels in a urine sample.

The above indicated markers are unique for IgAN and have been selected based on analysis of urine samples from patients suffering from IgAN, ADPKD, LN and healthy controls. It is herein disclosed that the levels of each protein and their non-full-length fragments, i.e. marker proteins truncated on one or both sides of the amino acid sequence of the complete protein, and/or the combination thereof correlate with the disease type, thus allowing for detection of IgAN in a patient, its differentiation from renal diseases having different etiology, and monitoring of the IgAN patient response to a treatment.

Accordingly, disclosed herein is a use of alpha-1B-glycoprotein (A1BG), alpha-1-acid glycoprotein 1 (ORM1), Ig lambda-2 chain C regions (IGLC2) and serotransferrin (TF), wherein said markers also comprise the non-full-length fragments thereof, as markers in diagnosis, monitoring and differentiation of IgAN. According to the invention at least two, three or four of the above identified makers, including the non-full-length fragments thereof, can be used for that purpose. Table 1 below lists the Uniprot ID accession numbers and summarizes the known functions for each of the marker selected according to the invention.

TABLE 1

The overview of the proteins being listed in the current invention

| No. | Name (gene symbol) | Uniprot ID | Molecular functions | Biological process |
|---|---|---|---|---|
| 1 | Alpha-1B-glycoprotein (A1BG) | P04217 | Not known | Not known |
| 2 | Alpha-1-acid glycoprotein 1 (ORM1) | P02763 | transport protein in the blood stream | acute-phase response, inflammatory response, transport |
| 3 | Ig lambda-2 chain C regions (IGLC2) | P0CG05 | antigen binding | Fc-epsilon receptor signaling pathway, complement activation, innate immune response |
| 4 | Serotransferrin (TF) | P02787 | ferric iron binding | transport |

Brief molecular and functional characteristics of each of the molecules reported are presented below:
1. Alpha-1B-glycoprotein (A1BG) is a 54.3 kDa protein in humans that is constituted of 495 amino acids and encoded by the A1BG gene localized in 19q13.43 (by Entrez Gene). The protein shows sequence similarity to the variable regions of some immunoglobulin supergene family member proteins and contains five Ig-like V-type (immunoglobulin-like) domains. The function of the protein in biological systems is yet to be established. It has been reported that A1BG protein can be a subject for fragmentation and that the 13.8 kDa A1BG fragment has a high discriminatory power for steroid resistance in pediatric nephrotic syndrome, but is only present in a subset of patients (see Piyaphanee N et al. Proteomics Clin Appl. 2011; 5:334-42).

2. Human Alpha-1-acid glycoprotein 1 (AGP1), also referred to as Orosomucoid 1 (ORM1), is a 41-43-kDa glycoprotein encoded by the gene localized in human genome at 9q32 (by Entrez Gene). In humans, the peptide moiety is a single chain of 201 amino acids of 23.5 kDa of molecular weight. Carbohydrates constitute approximately the remaining 45% of the molecular weight of the posttranslationally modified protein, attached in the form of five to six highly sialylated complex-type-N-linked glycans. AGP1 belongs to the family of acute phase proteins. Accordingly, its serum concentration increases in response to systemic tissue injury, inflammation or infection. This increase in serum concentration results primarily from an elevated protein production in liver, as a part of an acute phase response. Expression of the AGP1 gene is a subject of regulation by a combination of the major regulatory mediators of an acute phase response, i.e. a cytokine network containing mainly interleukin-1 beta (IL-1beta), tumor necrosis factor-alpha (TNFalpha), interleukin-6 and a range of IL-6-related cytokines as well as glucocorticoids. The biological function of AGP1 is not clear. The main known ability of AGP1 is to bind and to carry numerous basic and neutral lipophilic drugs from endogenous (e.g. steroid hormones) and exogenous (such as phenobarbital) origin. The primary factor influencing the immunomodulaatory or the binding activities of AGP1 is related to the composition of carbohydrates bound to AGP1 polypeptide.

3. Ig lambda-2 chain C regions (IGLC2) is encoded by a gene belonging to the gene family of the constant region of immunoglobulin lambda chains. The rearranged IGLC2 gene (localized at 22q11.2, by Entez gene) encodes the protein constituted of approximately 106 amino acids of a theoretical weight of approximately 11.2 kDa. The main function of IGLC2 protein in participation in antigen recognition and binding as well as subsequent initiation and regulation of antigen-specific immune response.

4. Serotransferrin (TF), also referred to as transferrin or siderophilin, is a ~80 kDa acute-phase serum glycoprotein responsible for transportation of $Fe^{3+}$ ions from sites of absorption and heme degradation to the sites of storage or degradation. The main site of production is liver, but this protein can be also produced in peripheral tissues. Serotransferrin plays a role in multiple processes in human body. In nephrotic syndrome, urinary loss of transferrin can be one of the causative mechanisms for an iron-resistant microcytic anemia. Used as a urine biomarker, serotransferrin has been reported one of the predictors of renal functional decline in lupus nephritis (see Abulaban K M et al. Lupus. 2016, in press).

In the first embodiment of the invention a method of diagnosis of IgA nephropathy in a subject is provided. This method of the invention comprises
(a) a step of identification of the of at least two, three or four of the markers selected from a group consisting of A1BG, ORM1, IGLC2 and TF, wherein said markers also comprise the non-full-length fragments thereof, in a urine sample from said subject and
(b) a step of quantitative or semi-quantitative comparison of the markers identified in step (a) with the markers identified in a healthy individual.

The term "a non-full length fragment" as used herein refers to marker proteins truncated on one or both sides of the amino acid sequence of the complete protein. A non-full length fragment of A1BG marker is any A1BG protein fragment having molecular weight lower than 85 kDa and preferably any protein having molecular weight of 13-60 kDa. More preferably, a non-full length fragment of A1BG marker is a middle range length fragment of 35-60 kDa and/or a bottom length fragment of 13-17 kDa. A non-full length fragment of TF marker is any TF protein fragment having molecular weight lower than 80 kDa and preferably any protein having molecular weight of 10-70 kDa. For other two markers no non-full length fragments were observed.

The term "quantitative comparison" refers to a comparison made using a quantitative measurement technique, wherein absolute amounts are measured. An example of such a technique includes mass spectrometry and ELISA. The term "semi-quantitative comparison" refers to a comparison made using a semi-quantitative measurement technique, wherein relative amounts are determined. An example of such a technique includes Western blot.

In said method of the invention a urine sample collected from a subject is analyzed, wherein said analysis comprises a step of separating all the solid parts from the sample, for example by filtration, centrifuging, or any other suitable method, and subsequently a step of identification of the of at least two, three or four of the markers selected from a group consisting of A1BG, ORM1, IGLC2 and TF, as well as their non-full length fragments, in said urine sample.

The presence of the markers in the urine sample in the method of the invention can be preferably determined by mass spectrometry (MS). In this aspect of the invention, the amino acid sequence can be identified based mass-to-charge ratio used to generate high-resolution mass spectra. An example of that method is presented in Example 1 below. In preferred aspect of this invention a tandem mass spectrometry (MS/MS) can be used as it was previously described, for example, in Aebersold R and Mann M, Nature, 2003, 422(6928), 198-207, and in Yates III J. R., Annual Review of Biophysics and Biomolecular Structure, 2004, 33, 297-316. Alternatively, different MS based technics can also be used to identify the above identified combinations of markers in urine samples (such as MALDI (matrix-assisted laser desorption) imaging mass spectrometry (MALDI-IMS), liquid chromatography-mass spectrometry (LC-MS), and electrospray ionization ESI MS and their combination), In a more preferred embodiment the combination of at least two, three or four of the markers selected from a group consisting of A1BG, ORM1, IGLC2 and TF, can be identified in said urine sample by ELISA-based methods, including microfluidic ELISA, protein electrophoresis and Western blotting, including microfluidic electrophoresis and Western blotting using capillary electrophoresis. These methods are well known in the art.

Ultrasensitive microfluidic solid-phase ELISA was reported and described, for example, in Lab Chip 2013; 13(21), 4190-4197. This method is useful in rapid and ultrasensitive quantitative detection of low abundance proteins. The microwell-based solid-phase ELISA strategy provides an expandable platform for developing the next-generation microfluidic immunoassay systems that integrate and automate digital and analog measurements to further improve the sensitivity, dynamic ranges, and reproducibility of proteomic analysis.

The other method, Microfluidic Electrophoresis Assays for Rapid Characterization of Protein, was characterized and discussed in Science/AAAS audio webinar (14.11.2012) by Dr. Joey Studts from Boehringer Ingelheim in Germany, Dr.

Timothy Blanc from ImClone Systems in Branchburg, N.J., and Dr. Bahram Fathollahi from PerkinElmer in San Francisco, Calif. What was discussed there concerned the application of high throughput microfluidic technologies to the analysis of biotherapeutic proteins. These microfluidic-based assays provide a good solution because they address the limitations of SDS-PAGE, as well as other separation assays that depend on conventional capillary electrophoresis in particularly analysis time, which can be reduced to a minute or less per sample. Advantages include miniaturization, integration, and automation, which enable labs to perform experiments at a rapid turnaround time, thus faster analytical analysis to reduce time and expense in the process development.

In publication Anal Chem. 2011; 83(4), 1350-1355 a microscale Western blotting system based on separating sodium-dodecyl sulfate protein complexes by capillary gel electrophoresis followed by deposition onto a blotting membrane for immunoassay was described by Anderson et al. In the system, the separation capillary is grounded through a sheath capillary to a mobile X-Y translation stage, which moves a blotting membrane past the capillary outlet for protein deposition. The obtained results demonstrate substantial reduction in time requirements and improvement in mass sensitivity compared to conventional Western blots. Western blotting using capillary electrophoresis shows promise to analyze low volume samples with reduced reagents and time, while retaining the information content of a typical Western blot.

The above described analysis method makes it possible to determine marker patterns useful in monitoring of a response of a patient to a treatment for IgAN and differentiation of IgAN from other chronic kidney diseases. The solution of the invention may eliminate the need to perform biopsy to confirm diagnosis of IgAN.

In a further embodiment a method of monitoring a response to an IgAN treatment is provided, wherein (a) in a first point in time the quantitative or semi-quantitative analysis of at least two, three or four of the markers selected from a group consisting of A1BG, ORM1, IGLC2 and TF, wherein said markers also comprise the non-full-length fragments thereof, in a urine sample of a subject is performed; (b) subsequently the same analysis is carried out at a later point of time, and (c) the response to the IgA nephropathy treatment is assessed based on comparison of the results obtained in step (a) and (b), wherein the lower marker expression is indicative of a response to the treatment response. In a preferred aspect of the invention steps (a) and (b) can be repeated.

The present invention also relates kit for diagnosis, differentiation and monitoring of IgA nephropathy in a subject, which comprises at least two antibodies that specifically bind to at least two markers selected from a group consisting of A1BG, ORM1, IGLC2 and TF, wherein said markers also comprise the non-full-length fragments thereof, and wherein said kit is equipped with means of identification of markers that bind the antibodies in said kit. The term "antibody"! "antibodies" includes also antibody fragments or derivatives that specifically bind the markers. The kit may determine or provide instructions for calculating a ratio or relationship between the markers. Further the antibody or antibodies in the kit of the invention may be conjugated to a label, such as a fluorophore or an enzyme or alternatively the kit can be provided with any other detection means known in the field, that enable identification of the markers bound to the antibodies. The antibody or antibodies in the kit of the invention may be comprised in a lateral flow device. In the most preferred embodiment the kit comprises a microfluidic chip. The kit may further comprise a package insert providing instructions for measuring the expression levels of the markers in a urine sample. The kit may further comprise instructions for determining the likelihood of developing a progressing or worsening IgAN in the subject.

The invention also provides the use of at least two, three or four of the markers selected from a group consisting of A1BG, ORM1, IGLC2 and TF for diagnosis, monitoring and differentiation of IgA nephropathy.

Any suitable combination of the above identified markers can be used according to the invention. Specific combinations of at least two, three or four of the markers selected from a group consisting of A1BG, ORM1, IGLC2 and TF are presented in FIG. 3.

In addition to the markers identified above, GP6 can be used as a marker, in accordance to the present invention, together with any suitable combination of markers as described above. Platelet glycoprotein VI (GP6) is a 58-kD platelet membrane protein playing a substantial function in the collagen-induced activation and aggregation of platelets. It acts as a major role player in vascular homeostasis and integrity. For instance, it has been shown that inhibition of platelet GP6 protects against myocardial ischemia-reperfusion injury (see Pachel C et al. Arterioscler Thromb Vasc Biol. 2016; 36(4):629-35). In relation to kidney diseases, platelet recruitment to the inflamed glomerulus, which is crucial in the pathogenesis of certain forms of glomerulonephritis, has been reported to occur via an alphaIIbbeta3/GPVI-dependent pathway (see Devi S, Am J Pathol. 2010; 177(3):1131-42).

BRIEF DESCRIPTION OF DRAWINGS

The invention was described in relation to the following figures of drawings in which FIG. 1 present sample results of Western blot analysis of A1BG, ORM1, IGLC2 and TF content in urine samples derived from patients with renal diseases versus healthy controls;

FIG. 7 presents a list of possible combinations of the markers for use according to the invention.

EXAMPLES

Example 1

Discovery Phase

Figure 1:
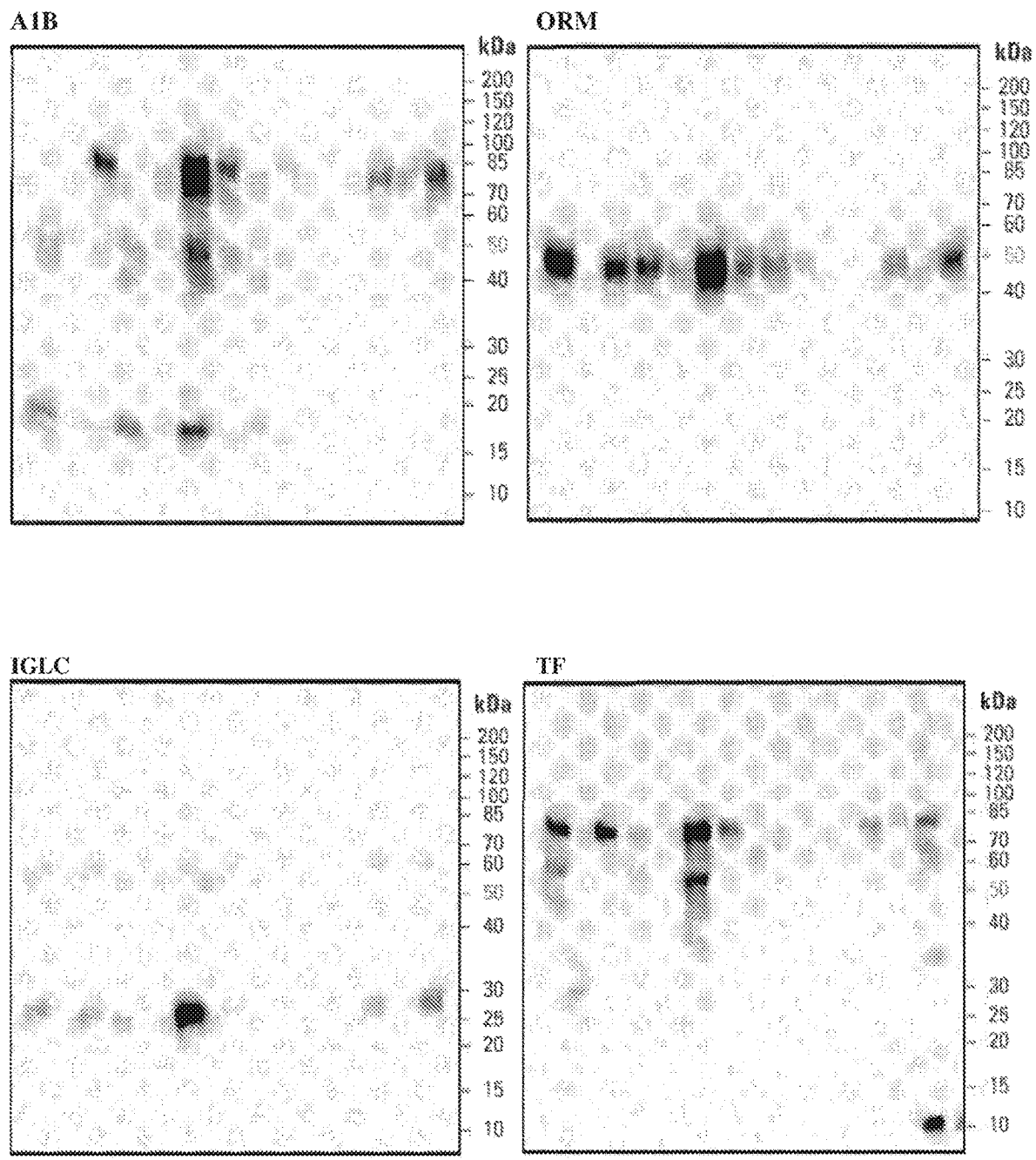

The methodological approach of the discovery phase has been described in Mucha et al. Below, the most pertinent information is listed.

Patients Characteristics

Groups of Patients

The study included 30 patients with IgAN and 30 healthy age- and sex-matched volunteers serving as controls. Demographic and clinical data of both groups are presented in Mucha, et al. (Supplementary material online, Table S1). Briefly, patients with biopsy-proven IgAN at different stages of chronic kidney disease (CKD) and older than 18 years were included. The inclusion criteria for the control group were as follows: age older than 18 years and absence of any kidney disease or other chronic diseases requiring treatment. The exclusion criteria for both groups included: active infection, history of malignancy, previous organ transplantation, or current pregnancy. To estimate GFR, we used the Chronic Kidney Disease Epidemiology Collaboration equations, which are the most accurate, have been evaluated in large diverse populations, and are applicable for clinical use. The study protocol was approved by the local ethics committee and informed consent was obtained from all participants. The study was performed in accordance with the Declaration of Helsinki.

Urine Collection

Samples were collected from all individuals according to a uniform study protocol, following the recommendations on urine proteomic sample collection. The second- or third-morning midstream urine was collected to sterile urine containers 1 to 3 h after previous urination. The pH of each sample was stabilized at 7.2 by addition of 1/10th vol. of 1M HEPES pH 7.2 immediately after collection. Then, samples were vortexed for 2 min, centrifuged at 3000×g at room temperature for 10 min to clear the debris, filtered (0.4-μm filter, Rotilabo-Spritzenfilter, Roth, Karlsruhe, Germany), and portioned into 1-ml aliquots that were stored at −80° C. before further use.

Sample Filtration

Membrane filters of the 10 kDa cut-off (Amicon Ultra-0.5, UFC501096, Millipore, Billerica, United States) were washed twice with MilliQ (MQ) water prior to use. Urine was centrifuged through the membrane at 14,000×g for 15 min. Next, 500 μl MQ was added to the retentate and centrifugation step was repeated. To recover the concentrated and desalted sample, the filter was placed upside down and centrifuged in a clean microcentrifuge tube for 2 min at 1000×g. The protein concentration was measured by the Bradford method. Aliquots of samples were stored at −80° C.

Sample Preparation

30 IgAN samples were divided into 3 disease pooled samples (DPSs I, II, and III), and similarly, 30 control samples were divided into 3 control pooled samples (CPSs I, II, and III). Age and sex matching was preserved within the 3 pairs of pooled sample groups. All DPSs and CPSs were obtained in 2 technical replicates (marked A and B) each, making a set of 12 pooled samples to be compared after isobaric tags for relative and absolute quantitation (iTRAQ) labeling. As 4-plex iTRAQ was used, 2 technical replications of DPSs and CPSs were compared in 1 isoelectric focusing/liquid chromatography-mass spectrometry/mass spectrometry (IEF/LC-MS/MS) experiment. To analyze 12 samples, we conducted a set of 3 independent IEF/LC-MS/MS experiments. Aliquots with extracted peptides were stored at −80° C. for the IEF/LC-MS/MS analysis.

Mass Spectrometry

Qualitative MS/MS data processing The MS/MS data were pre-processed with Mascot Distiller (v. 2.3.2.0, Matrix Science, London, United Kingdom). Data search using the MASCOT search engine was conducted on the Swiss-Prot database with the taxonomy restricted to *Homo sapiens* (20,236 sequences) in a 3-step procedure described elsewhere to calculate MS and MS/MS measurement errors and to recalibrate the data for the repeated MASCOT to remove systematic bias. Protein ratios were calculated as the median ratio of their peptide's ratios. The statistical significance of a single protein ratio was assessed by an in-house program, Diffprot. Calculated P values were adjusted for multiple testing using a false discovery rate-con-trolling procedure, yielding protein ratio q values.

Results of the Discovery Phase

As a result of qualitative analysis (peptide and protein identification) in each of the 3 IEF/LC-MS-MS/MS experiments, 761, 951, and 956 proteins were identified, respectively, each represented by 2 or more peptides. The results of this observations were partially presented in Mucha et al. The discovery of alpha-1B-glycoprotein (A1BG), alpha-1-acid glycoprotein 1 (AGP1, ORM1), Ig lambda-2 chain C regions (IGLC2) and serotransferrin (TF) as markers for IgAN is being reported in the current invention (Table 2).

TABLE 2

Peptide read-outs of urine proteomics specific for alpha-1B-glycoprotein (A1BG), alpha-1-acid glycoprotein 1 (AGP1, ORM1), Ig lambda-2 chain C regions (IGLC2) and serotransferrin (TF) obtained in a discovery phase of the invention.

| ID 1 | Protein name | Gene | Number of peptides |
|---|---|---|---|
| P04217 | Alpha-1B-glycoprotein | A1BG | 51 |
|  | Peptides | q-value |  |
| SEQ ID NO: 1 | SLPAPW | 4.26E-03 |  |
| SEQ ID NO: 2 | ITPGLK | 4.66E-03 |  |
| SEQ ID NO: 3 | GVTFLLR | 2.84E-03 |  |

TABLE 2-continued

Peptide read-outs of urine proteomics specific for alpha-1B-glycoprotein (A1BG), alpha-1-acid glycoprotein 1 (AGP1, ORM1), Ig lambda-2 chain C regions (IGLC2) and serotransferrin (TF) obtained in a discovery phase of the invention.

| | | |
|---|---|---|
| SEQ ID NO: 4 | SWVPHTF | 5.71E-03 |
| SEQ ID NO: 5 | LLELTGPK | 0.00E+00 |
| SEQ ID NO: 6 | SWITPGLK | 4.57E-04 |
| SEQ ID NO: 7 | ATWSGAVLAGR | 0.00E+00 |
| SEQ ID NO: 8 | LELHVDGPPPR | 7.51E-04 |
| SEQ ID NO: 9 | SLPAPWLSMAPV | 0.00E+00 |
| SEQ ID NO: 10 | VAPLSGVDFQLR | 0.00E+00 |
| SEQ ID NO: 11 | IFVGPQHAGNYR | 6.31E-05 |
| SEQ ID NO: 12 | HQFLLTGDTQGR | 0.00E+00 |
| SEQ ID NO: 13 | LETPDFQLFK | 0.00E+00 |
| SEQ ID NO: 14 | SGLSTGWTQLSK | 0.00E+00 |
| SEQ ID NO: 15 | SMAPVSWITPGLK | 1.67E-03 |
| SEQ ID NO: 16 | HGESSQVLHPGNK | 0.00E+00 |
| SEQ ID NO: 17 | SLPAPWLSMAPVSW | 6.55E-03 |
| SEQ ID NO: 18 | LELHVDGPPPRPQL | 3.58E-04 |
| SEQ ID NO: 19 | HHGESSQVLHPGNK | 7.56E-05 |
| SEQ ID NO: 20 | HQFLLTGDTQGRYR | 7.25E-03 |
| SEQ ID NO: 21 | GVAQEPVHLDSPAIK | 0.00E+00 |
| SEQ ID NO: 22 | LELIFVGPQHAGNYR | 0.00E+00 |
| SEQ ID NO: 23 | LELHVDGPPPRPQLR | 2.78E-04 |
| SEQ ID NO: 24 | IFFHLNAVALGDGGHY | 0.00E+00 |
| SEQ ID NO: 25 | NLELIFVGPQHAGNYR | 0.00E+00 |
| SEQ ID NO: 26 | TFESELSDPVELLVAES | 7.70E-04 |
| SEQ ID NO: 27 | GAAANLELIFVGPQHAGNYR | 0.00E+00 |
| SEQ ID NO: 28 | SLPAPWLSMAPVSWITPGLK | 0.00E+00 |
| SEQ ID NO: 29 | TPGAAANLELIFVGPQHAGNYR | 0.00E+00 |
| SEQ ID NO: 30 | SWVPHTFESELSDPVELLVAES | 0.00E+00 |
| SEQ ID NO: 31 | TVRTPGAAANLELIFVGPQHAGNYR | 0.00E+00 |
| SEQ ID NO: 32 | LHDNQNGWSGDSAPVELILSDETLPAPEFSPEPESGR | 1.74E-03 |
| SEQ ID NO: 33 | TDGEGALSEPSATVTIEELAAPPPPVLMHHGESSQVLHPGNK | 0.00E+00 |
| SEQ ID NO: 34 | SWVPHTFE | 6.44E-03 |
| SEQ ID NO: 35 | VGPQHAGNYR | 6.31E-05 |
| SEQ ID NO: 36 | STGWTQLSK | 9.51E-03 |
| SEQ ID NO: 37 | HQFLLTGDTQ | 0.00E+00 |
| SEQ ID NO: 38 | PVSWITPGLK | 0.00E+00 |
| SEQ ID NO: 39 | HVDGPPPRPQLR | 1.02E-03 |
| SEQ ID NO: 40 | LSMAPVSWITPGLK | 6.31E-05 |
| SEQ ID NO: 41 | MHHGESSQVLHPGNK | 3.73E-04 |

TABLE 2-continued

Peptide read-outs of urine proteomics specific for alpha-1B-glycoprotein (A1BG), alpha-1-acid glycoprotein 1 (AGP1, ORM1), Ig lambda-2 chain C regions (IGLC2) and serotransferrin (TF) obtained in a discovery phase of the invention.

| | | |
|---|---|---|
| SEQ ID NO: 42 | SGLSTGWTQLSKLLELTGPK | 3.87E-05 |
| SEQ ID NO: 43 | GPPPRPQLR | 7.28E-03 |
| SEQ ID NO: 44 | SLPAPWLSMA | 5.85E-04 |
| SEQ ID NO: 45 | LELHVDGPPPRPQ | 4.34E-04 |
| SEQ ID NO: 46 | IFFHLNAVALGDGGH | 0.00E+00 |
| SEQ ID NO: 47 | NGVAQEPVHLDSPAIK | 3.87E-05 |
| SEQ ID NO: 48 | TPGAAANLELIFVGPQHAGN | 0.00E+00 |
| SEQ ID NO: 49 | LPAPWLSMAPVSWITPGLK | 3.87E-05 |

| ID 2 | Protein name | Gene | Number of peptides |
|---|---|---|---|
| P02763 | Alpha-1-acid glycoprotein 1 | ORM1 | 29 |
| | Peptides | q-value | |
| SEQ ID NO: 50 | TYMLAF | 1.964E-03 | |
| SEQ ID NO: 51 | AHLLILR | 0.000E+00 | |
| SEQ ID NO: 52 | NWGLSVY | 6.310E-05 | |
| SEQ ID NO: 53 | TYLNVQR | 5.215E-03 | |
| SEQ ID NO: 54 | YVGGQEHF | 6.264E-03 | |
| SEQ ID NO: 55 | FAHLLILR | 1.789E-04 | |
| SEQ ID NO: 56 | TTYLNVQR | 4.565E-04 | |
| SEQ ID NO: 57 | YVGGQEHFA | 5.451E-04 | |
| SEQ ID NO: 58 | YVGGQEHFAH | 0.000E+00 | |
| SEQ ID NO: 59 | EHFAHLLILR | 6.704E-03 | |
| SEQ ID NO: 60 | SDVVYTDWK | 0.000E+00 | |
| SEQ ID NO: 61 | YVGGQEHFAHL | 0.000E+00 | |
| SEQ ID NO: 62 | MLAFDVNDEK | 0.000E+00 | |
| SEQ ID NO: 63 | YVGGQEHFAHLL | 3.866E-05 | |
| SEQ ID NO: 64 | GQEHFAHLLILR | 0.000E+00 | |
| SEQ ID NO: 65 | SVYADKPETTK | 0.000E+00 | |
| SEQ ID NO: 66 | TYMLAFDVNDEK | 0.000E+00 | |
| SEQ ID NO: 67 | GLSVYADKPETTK | 3.866E-05 | |
| SEQ ID NO: 68 | EQLGEFYEALDCLR | 0.000E+00 | |
| SEQ ID NO: 69 | YVGGQEHFAHLLILR | 0.000E+00 | |
| SEQ ID NO: 70 | WGLSVYADKPETTK | 3.866E-05 | |
| SEQ ID NO: 71 | NWGLSVYADKPETTK | 0.000E+00 | |
| SEQ ID NO: 72 | DVNDEKNWGLSVYADKPETTK | 0.000E+00 | |
| SEQ ID NO: 73 | TYMLAFDVNDEKNWGLSVYADKPETTK | 0.000E+00 | |
| SEQ ID NO: 74 | VVYTDWK | 7.322E-03 | |
| SEQ ID NO: 75 | VYADKPETTK | 1.877E-03 | |

TABLE 2-continued

Peptide read-outs of urine proteomics specific for alpha-1B-glycoprotein (A1BG), alpha-1-acid glycoprotein 1 (AGP1, ORM1), Ig lambda-2 chain C regions (IGLC2) and serotransferrin (TF) obtained in a discovery phase of the invention.

| | | |
|---|---|---|
| SEQ ID NO: 76 | VGGQEHFAHLLILR | 2.390E-04 |
| SEQ ID NO: 77 | IPKSDVVYTDWK | 6.846E-03 |
| SEQ ID NO: 78 | GGQEHFAHLLILR | 3.901E-03 |

| ID 3 | Protein name | Gene | Number of peptides |
|---|---|---|---|
| P0CG05 | Ig lambda-2 chain C regions | IGLC2 | 4 |
| | Peptides | q-value | |
| SEQ ID NO: 79 | ADSSPVK | 5.85E-04 | |
| SEQ ID NO: 80 | GVETTTPSK | 1.61E-04 | |
| SEQ ID NO: 81 | AGVETTTPSK | 0.00E+00 | |
| SEQ ID NO: 82 | KAGVETTTPSK | 8.03E-04 | |

| ID 4 | Protein name | Gene | Number of peptides |
|---|---|---|---|
| P02787 | Serotransferrin | TF | 76 |
| | Peptides | q-value | |
| SEQ ID NO: 83 | VYIAGK | 4.49E-03 | |
| SEQ ID NO: 84 | DSGFQMN | 1.79E-04 | |
| SEQ ID NO: 85 | HSTIFEN | 1.05E-03 | |
| SEQ ID NO: 86 | GLLYNK | 3.85E-03 | |
| SEQ ID NO: 87 | SAGWNIPI | 9.31E-03 | |
| SEQ ID NO: 88 | PDPWAK | 5.33E-03 | |
| SEQ ID NO: 89 | MYLGYEY | 4.17E-04 | |
| SEQ ID NO: 90 | NPDPWAK | 1.79E-04 | |
| SEQ ID NO: 91 | DSAHGFLK | 0.00E+00 | |
| SEQ ID NO: 92 | FGYSGAFK | 2.78E-04 | |
| SEQ ID NO: 93 | VAEFYGSK | 0.00E+00 | |
| SEQ ID NO: 94 | KDSGFQMN | 9.23E-04 | |
| SEQ ID NO: 95 | EFQLFSSPH | 2.43E-04 | |
| SEQ ID NO: 96 | KPVEEYAN | 6.13E-04 | |
| SEQ ID NO: 97 | DGAGDVAFVK | 0.00E+00 | |
| SEQ ID NO: 98 | SAGWNIPIGLL | 0.00E+00 | |
| SEQ ID NO: 99 | EDLIWELLN | 3.73E-04 | |
| SEQ ID NO: 100 | YLGEEYVK | 3.87E-05 | |
| SEQ ID NO: 101 | HSTIFENLAN | 0.00E+00 | |
| SEQ ID NO: 102 | GYYGYTGAFR | 0.00E+00 | |
| SEQ ID NO: 103 | KPVDEYK | 4.57E-04 | |
| SEQ ID NO: 104 | IPMGLLYNK | 3.87E-05 | |
| SEQ ID NO: 105 | DSGFQMNQLR | 0.00E+00 | |
| SEQ ID NO: 106 | PVVAEFYGSK | 0.00E+00 | |
| SEQ ID NO: 107 | LAQVPSHTVVAR | 0.00E+00 | |
| SEQ ID NO: 108 | KPVDEYKD | 8.27E-04 | |

TABLE 2-continued

Peptide read-outs of urine proteomics specific for alpha-1B-glycoprotein (A1BG), alpha-1-acid glycoprotein 1 (AGP1, ORM1), Ig lambda-2 chain C regions (IGLC2) and serotransferrin (TF) obtained in a discovery phase of the invention.

| | | |
|---|---|---|
| SEQ ID NO: 109 | EGYYGYTGAFR | 3.87E-05 |
| SEQ ID NO: 110 | SAGWNIPIGLLY | 6.31E-05 |
| SEQ ID NO: 111 | NIPMGLLYNK | 2.78E-04 |
| SEQ ID NO: 112 | HQTVPQNTGGK | 0.00E+00 |
| SEQ ID NO: 113 | QYFGYSGAFK | 6.31E-05 |
| SEQ ID NO: 114 | TAGWNIPMGLLY | 6.31E-05 |
| SEQ ID NO: 115 | SLDGGFVYIAGK | 0.00E+00 |
| SEQ ID NO: 116 | SASDLTWDNLK | 0.00E+00 |
| SEQ ID NO: 117 | HSTIFENLANK | 0.00E+00 |
| SEQ ID NO: 118 | EFQLFSSPHGK | 0.00E+00 |
| SEQ ID NO: 119 | TAGWNIPMGLLYN | 3.87E-05 |
| SEQ ID NO: 120 | SKEFQLFSSPH | 2.29E-03 |
| SEQ ID NO: 121 | KDSGFQMNQLR | 0.00E+00 |
| SEQ ID NO: 122 | EDLIWELLNQAQ | 1.61E-04 |
| SEQ ID NO: 123 | MYLGYEYVTAIR | 0.00E+00 |
| SEQ ID NO: 124 | KEGYYGYTGAFR | 0.00E+00 |
| SEQ ID NO: 125 | LKPVVAEFYGSK | 0.00E+00 |
| SEQ ID NO: 126 | KSASDLTWDNLK | 0.00E+00 |
| SEQ ID NO: 127 | TAGWNIPMGLLYNK | 0.00E+00 |
| SEQ ID NO: 128 | STLNQYFGYSGAFK | 6.31E-05 |
| SEQ ID NO: 129 | NLKPVVAEFYGSK | 0.00E+00 |
| SEQ ID NO: 130 | EDPQTFYYAVAVVK | 0.00E+00 |
| SEQ ID NO: 131 | SKEFQLFSSPHGK | 0.00E+00 |
| SEQ ID NO: 132 | AIAANEADAVTLDAGLVYDAY | 0.00E+00 |
| SEQ ID NO: 133 | LAPNNLKPVVAEFYGSK | 0.00E+00 |
| SEQ ID NO: 134 | EDLIWELLNQAQEHFGK | 0.00E+00 |
| SEQ ID NO: 135 | IMNGEADAMSLDGGFVYIAGK | 3.87E-05 |
| SEQ ID NO: 136 | AIAANEADAVTLDAGLVYDAYLAPN | 0.00E+00 |
| SEQ ID NO: 137 | GKEDLIWELLNQAQEHFGK | 0.00E+00 |
| SEQ ID NO: 138 | GGKEDLIWELLNQAQEHFGK | 0.00E+00 |
| SEQ ID NO: 139 | EDLIWELLNQAQEHFGKDK | 0.00E+00 |
| SEQ ID NO: 140 | SMGGKEDLIWELLNQAQEHFGK | 0.00E+00 |
| SEQ ID NO: 141 | AIAANEADAVTLDAGLVYDAYLAPNNLKPVVAEFYGSK | 0.00E+00 |
| SEQ ID NO: 142 | APNHAVVT | 8.70E-03 |
| SEQ ID NO: 143 | APNHAVVTR | 6.31E-05 |
| SEQ ID NO: 144 | SAGWNIPIGL | 8.24E-03 |
| SEQ ID NO: 145 | QVPSHTVVAR | 1.06E-03 |
| SEQ ID NO: 146 | STIFENLANK | 0.00E+00 |

TABLE 2-continued

Peptide read-outs of urine proteomics specific for alpha-1B-glycoprotein (A1BG), alpha-1-acid glycoprotein 1 (AGP1, ORM1), Ig lambda-2 chain C regions (IGLC2) and serotransferrin (TF) obtained in a discovery phase of the invention.

| | | |
|---|---|---|
| SEQ ID NO: 147 | HLAQVPSHTVVAR | 0.00E+00 |
| SEQ ID NO: 148 | GWNIPMGLLYNK | 6.31E-05 |
| SEQ ID NO: 149 | MYLGYEYVTAIRNLR | 3.86E-03 |
| SEQ ID NO: 150 | PNNLKPVVAEFYGSK | 5.33E-03 |
| SEQ ID NO: 151 | HSTIFENLA | 5.85E-04 |
| SEQ ID NO: 152 | ADRDQYELL | 1.81E-03 |
| SEQ ID NO: 153 | QLFSSPHGK | 1.75E-03 |
| SEQ ID NO: 154 | LGYEYVTAIR | 2.69E-03 |
| SEQ ID NO: 155 | HSTIFENLANKADR | 5.85E-04 |
| SEQ ID NO: 156 | HQTVPQNTGGKNPDPWAK | 3.87E-05 |
| SEQ ID NO: 157 | KEDLIWELLNQAQEHFGK | 1.52E-03 |
| SEQ ID NO: 158 | GLVYDAYLAPNNLKPVVAEFYGSK | 3.87E-05 |

Example 2

Validation Phase

The primary difference between the discovery and validation phases is the transition from the assessment of the pooled urine samples (i.e. the discovery phase) to the individual evaluation of each protein in a given patient or a healthy person and a direct correlation of these results with the known clinical parameters in each case (i.e. the validation phase).

Patient Characteristics

The study included 133 renal disease patients and 19 healthy controls. Renal disease included IgAN (77 cases), ADPKD (29) and LN (27).

Sample Collection

Urinary samples were collected according to the protocol standardized in the Transplantation Institute, Medical University of Warsaw.

SDS-PAGE

Samples were defrozen to room temperature (~23° C.), then suspended by intensive pipetting or mixing using a vortex. Leammli buffer was added to urine samples to achieve final concentrations as follows: 2% SDS; 10% glycerol; 5% β-mercaptoethanol; 0.002% bromophenol blue; 0.125 M Tris-HCl; pH 6.8. Samples were boiled at 95° C. for 2 min. 10 μl of each sample was loaded on the Mini-PROTEAN TGX 4-15% gradient gel.

Western Blotting Analysis

The method developed by the Department of Molecular Biology, Institute of Biochemistry and Biophysics, Polish Academy of Sciences (patent application no P.415033) allows to assay all the proteins of interest in the urine samples. It permits the analysis of all the selected protein biomarkers with the accuracy not reachable by classical methods. To date, the proteome analysis of urine in medicine starts from centrifugation of the sample (in line with the European Confederacy of Laboratory Medicine guidelines), which result losing of protein which are insoluble, and exist as aggregates or degradants. This solid fraction is crucial because proteins progress into insoluble forms randomly, depending of protein, state of patient, his diet and properties of urine. For that reason, in the current study we used the whole urine in form of suspension, which next were analyzed by Western blotting technique. That gives an opportunity to examine all of proteins present in a given in urine sample. Advantages of this method are important for medicinal diagnostics. Method is noninvasive for patients, it allows collecting the samples from the patients even few times per day, and it is relatively little time consuming. For Western blotting analysis, the urine protein samples were separated on SDS-PAGE gels, as described above, and transferred to a nitrocellulose membrane. Membranes were incubated in appropriate blocking buffer (either 5% low-fat dry milk or bovine serum albumin in TBS-TWEEN® 20 (polysorbate 20) (TBST)). After an incubation in the primary antibody (A1BG (F-9); catalog number sc-374415; Santa Cruz) the cells were washed in TBST, and incubated with a horseradish peroxidase-conjugated secondary antibody. The chemiluminescence reaction for HRP was developed using SuperSignal West Femto Chemiluminescent Substrate (Thermo Scientific) and visualized with Stella 8300 bioimager. Densitometry read-outs were carried out for each of the bands in the blots. Eight randomly chosen patients samples were pooled together and used on each Western blot as a benchmark. Densitometry read-outs from other band on a given Western blot membrane were divided by the read-out of the respective benchmark. The results were referred to as a "relative band density".

List of antibodies used for Western blotting: A1BG (cat #sc-374415, Santa Cruz), ORM1 (sc-69753, Santa Cruz), IGLC2 (sc-33134, Santa Cruz), TF (sc-21011, Santa Crus), GP6 (sc-20149, Santa Cruz).

Results

The results of representative Western blotting analysis for A1BG, ORM1, IGLC2 and TF presence in urine samples are presented in FIG. 1.

Figure 2:
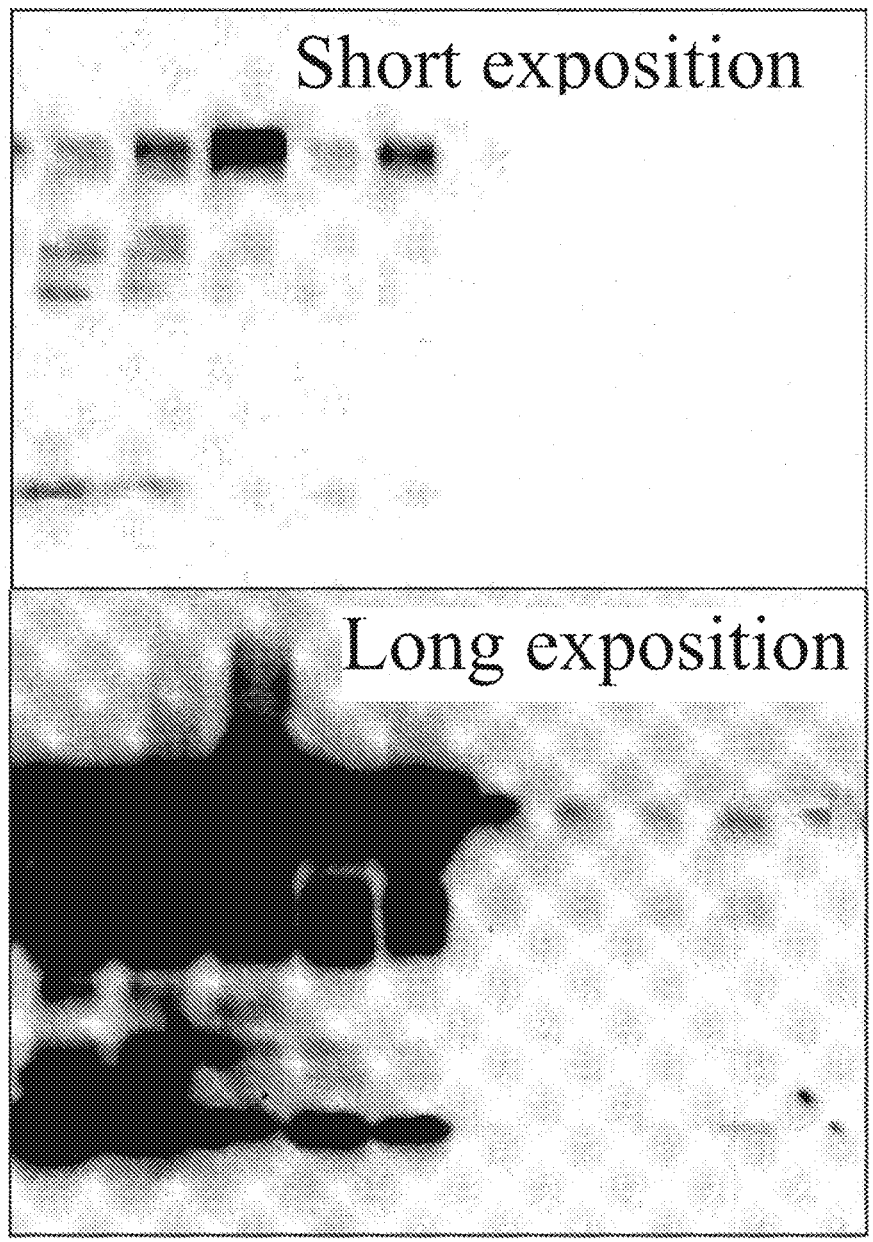
FIG. 2A shows evaluation by Western blotting of the A1BG protein in selected urine samples of study participants with renal diseases (left-hand side of the blots) as compared to healthy subjects (right hand side of the blots). The presence of several subforms of the protein within various molecular weight can be noticed. Densitometry measurements were done for the upper, middle and bottom ranges separately.
As shown in FIG. 2B, each of the molecular ranges correlated differently with the clinical diagnosis and also as compared to the cumulative assessment of all ranges (FIG. 2C)
Figure 2:
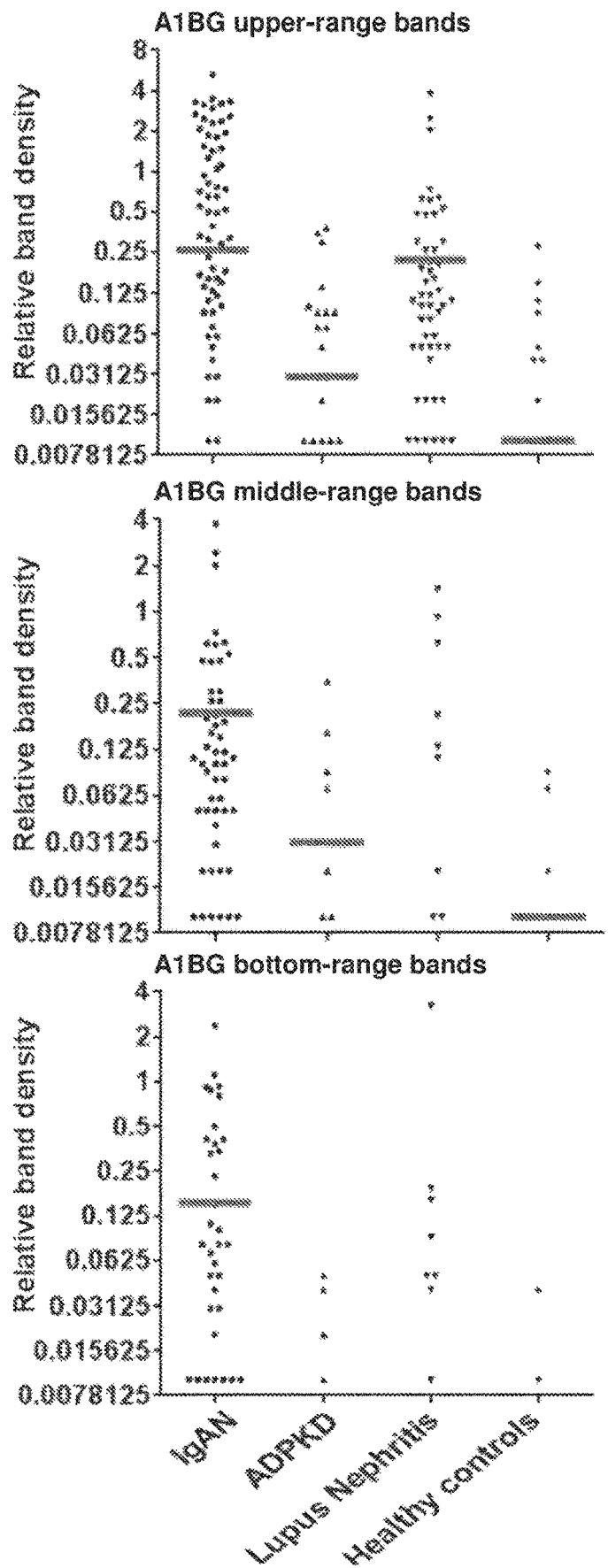
Figure 2:
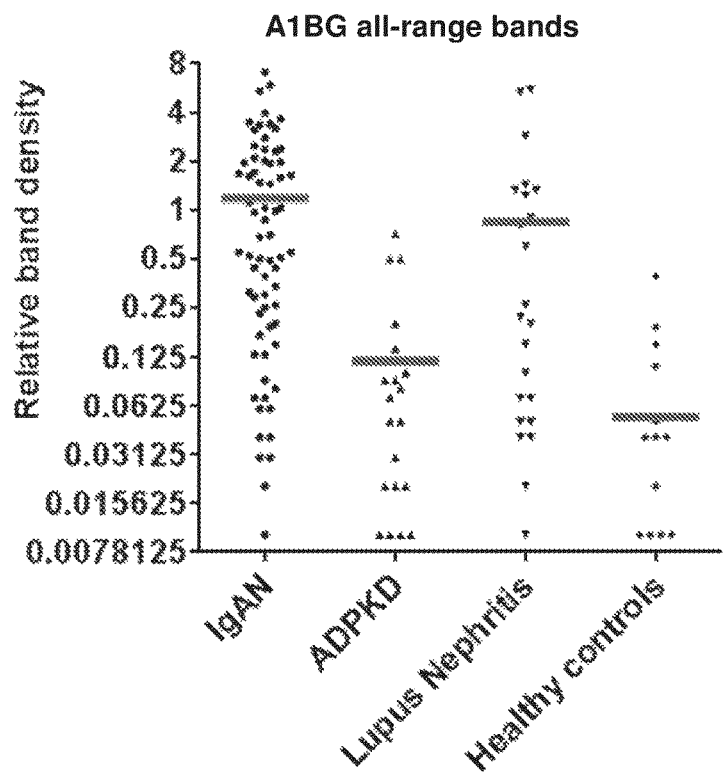

A1BG Based on the Western blotting analysis, it becomes evident that study participants with kidney diseases exhibit the presence of different forms of the protein (for the purpose of this invention segregated into within the high [~80 kDa], medium [~45 kDa] and low [~15 kDa] molecular weight range), occurring in different proportions. A direct comparison of selected samples from kidney disease versus heathy patients is presented in FIG. 2A. Mutual relations between the visible forms may be important in the pathophysiology of the given disease. Indeed, as presented in FIG. 2B, various subforms of A1BG correlate differently with the type of kidney disease and also differently as compared to the cumulative assessment of the protein (FIG. 2C). Notably, the bottom-range bands tend to be most prominently elevated in IgAN patients.

Figure 3:
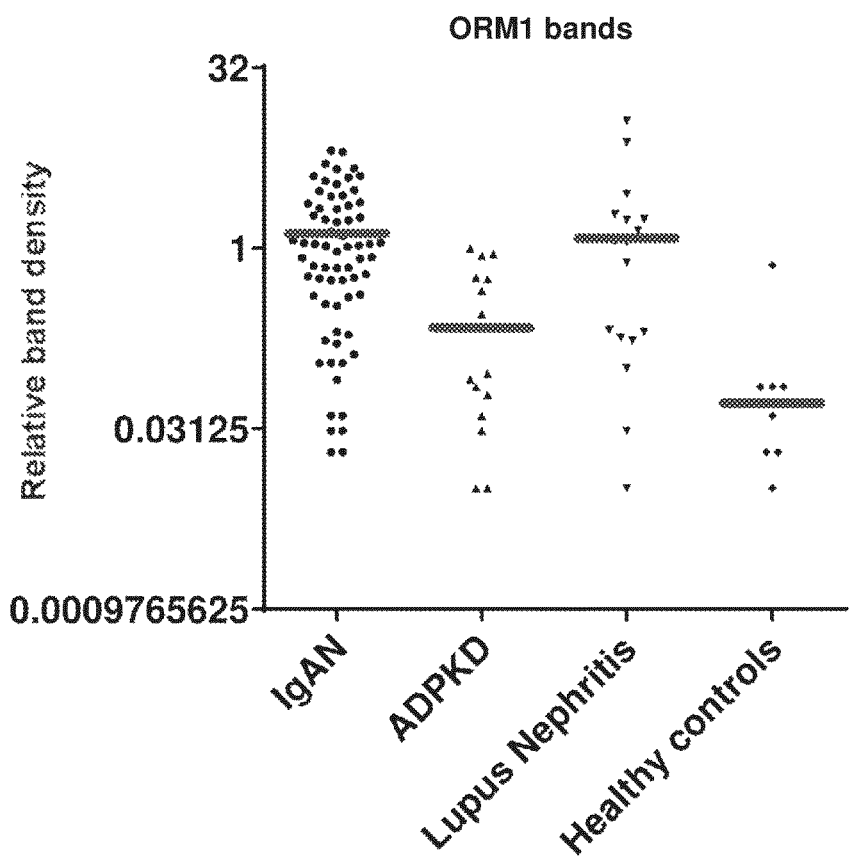
FIG. 3 shows a summary of densitometry readings from Western blotting of the ORM1 protein in selected urine samples of study participants with renal diseases as compared to healthy subjects.
Figure 4:
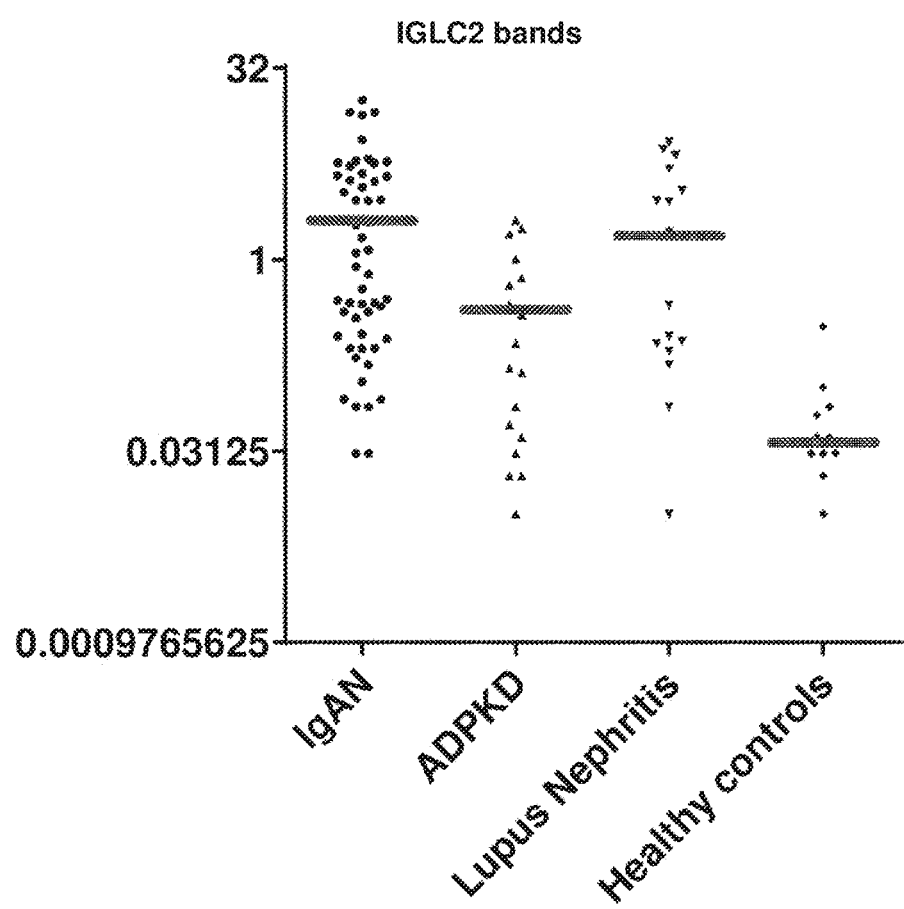
FIG. 4 shows a summary of densitometry readings from Western blotting of the IGLC2 protein (~30 kDa) in selected urine samples of study participants with renal diseases as compared to healthy subjects.
Figure 5:
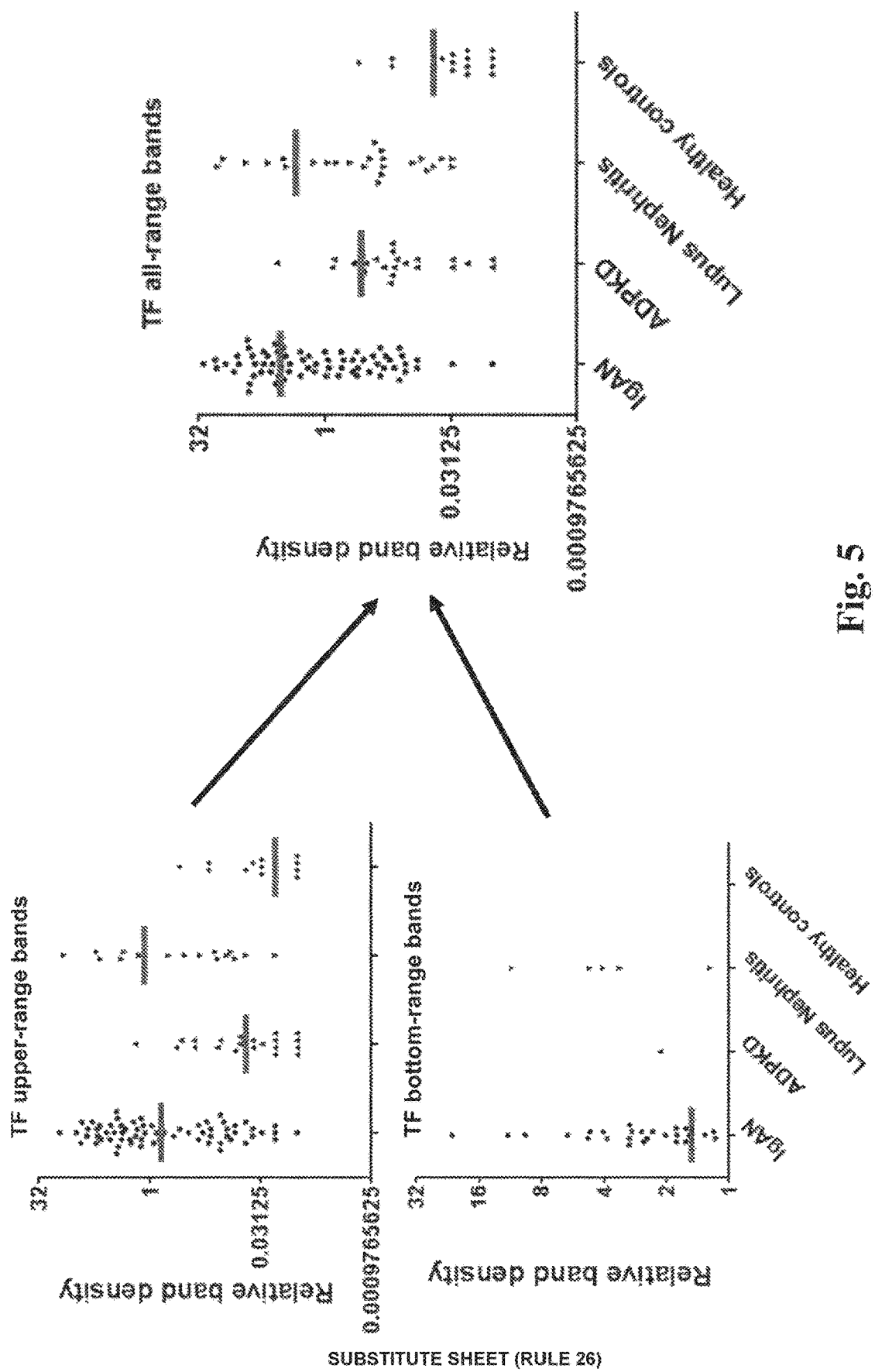
FIG. 5 shows a summary of densitometry readings from Western blotting of the TF protein in selected urine samples of study participants with renal diseases as compared to healthy subjects.
Figure 6:
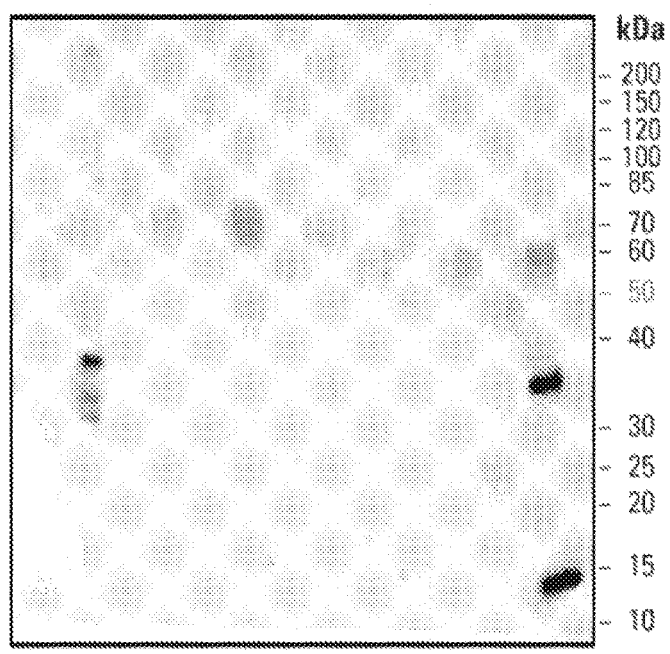
FIG. 6(A) present sample results of Western blot analysis of GP6 content in urine samples derived from patients with renal diseases versus healthy controls, and (B) shows a summary of densitometry readings from Western blotting of the GP6 protein in selected urine samples of study participants with renal diseases as compared to healthy subjects.
Figure 6B:
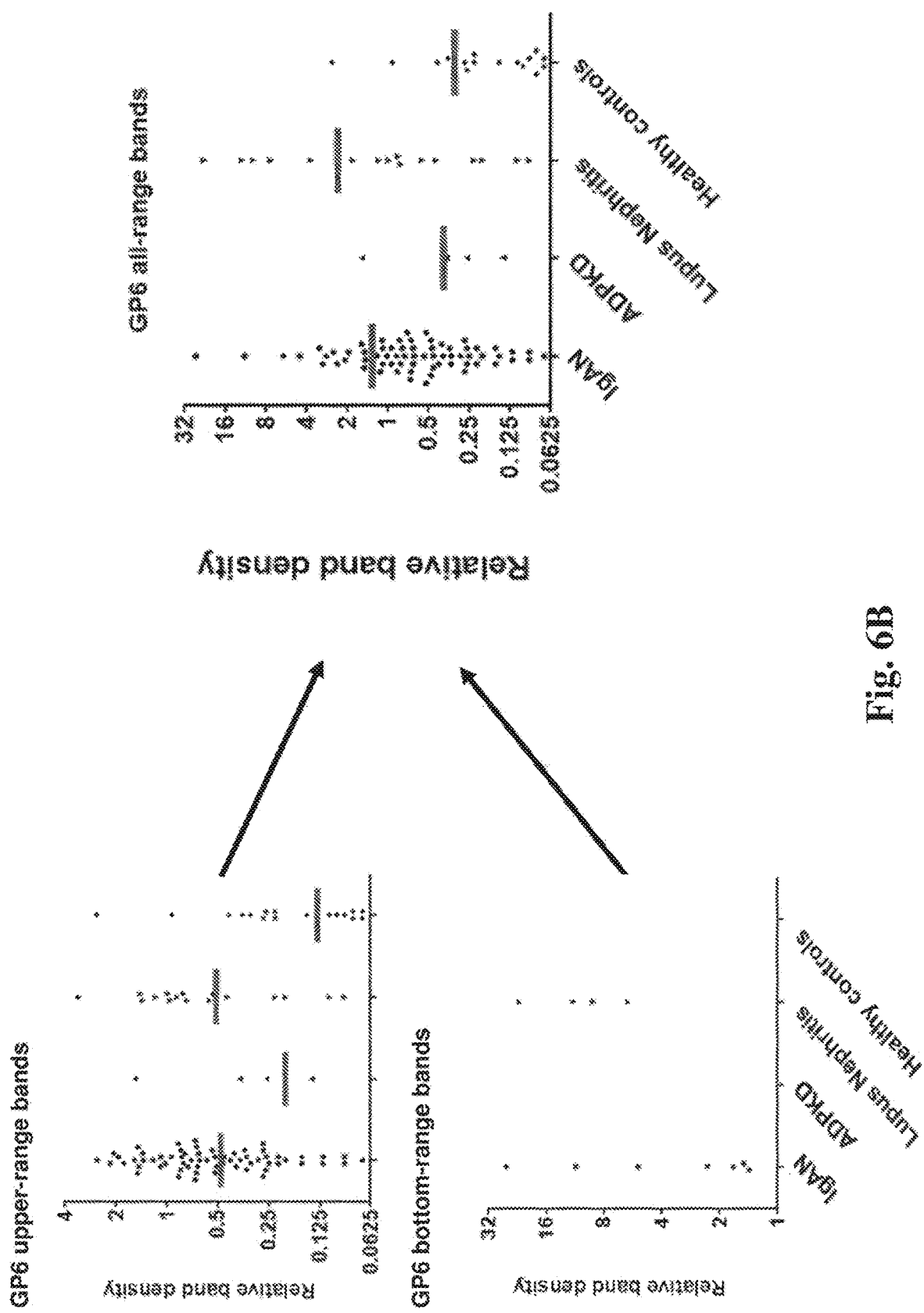

Validation phase as described above was also performed for the other markers, in particular ORM1, IGLC2 and TF and the results are presented in FIGS. 3-5. The results are also presented for GP6 (FIG. 6). Although GP6 is on average expressed at higher levels in LN than IgA, on the basis of our results and data, the compilation of 4 proteins reported in the GP6 compilation may increase the sensitivity and specificity of the test.

The invention claimed is:

1. A method of diagnosis of IgA nephropathy in a human subject, comprising:
   (a) a step of detecting a combination of alpha-1B-glycoprotein (A1BG), orosomucoid 1 (ORMI), and Ig lambda-2 chain C regions (IGLC2) as protein markers in a urine sample from said human subject, wherein the markers are detected as peptide fragments using mass spectrometry;
   (b) a step of quantitative or semi-quantitative comparison of the markers detected in step (a) with the markers detected in a urine sample from a healthy human individual; and
   (c) a step of correlating results obtained in step (b) with the presence of IgA nephropathy in the human subject if the levels of all markers in the examined sample from the human subject identified in step (a) are higher than the levels of the same markers present the sample from the healthy human individual.

2. The method of claim 1, wherein a serotransferrin (TF) or platelet glycoprotein VI (GP6) as a further marker is detected and compared.

3. The method of claim 1, wherein the markers are detected using mass spectrometry in combination with an antibody-based test.

4. The method of claim 3, wherein the antibody-based test is Western blot.

* * * * *